(12) United States Patent
Kobayashi et al.

(10) Patent No.: US 7,439,407 B2
(45) Date of Patent: Oct. 21, 2008

(54) FLUORINATED PENTACENE DERIVATIVE AND METHOD OF PRODUCING SAME

(75) Inventors: Masafumi Kobayashi, Shibukawa (JP); Osamu Omae, Shibukawa (JP); Kimitaka Ohkubo, Shibukawa (JP); Yuan Gao, Shibukawa (JP)

(73) Assignee: Kanto Denka Kogyo Co., Ltd., Tokyo (JP)

( * ) Notice: Subject to any disclaimer, the term of this patent is extended or adjusted under 35 U.S.C. 154(b) by 254 days.

(21) Appl. No.: 10/578,259

(22) PCT Filed: Nov. 2, 2004

(86) PCT No.: PCT/JP2004/016248

§ 371 (c)(1),
(2), (4) Date: May 4, 2006

(87) PCT Pub. No.: WO2005/042445

PCT Pub. Date: May 12, 2005

(65) Prior Publication Data

US 2007/0083067 A1    Apr. 12, 2007

(30) Foreign Application Priority Data

Nov. 4, 2003    (JP)    ............... 2003-373970

(51) Int. Cl.
*C07C 25/22*    (2006.01)
*C07C 17/18*    (2006.01)
*C07C 17/23*    (2006.01)
*C07C 23/18*    (2006.01)
*C07C 45/63*    (2006.01)
*C07C 46/00*    (2006.01)
*C07C 49/697*   (2006.01)
*C07C 50/36*    (2006.01)
*C07B 61/00*    (2006.01)

(52) U.S. Cl. ............... 570/129; 568/309; 568/326; 568/331; 568/332; 568/333

(58) Field of Classification Search ............ None
See application file for complete search history.

(56) References Cited

OTHER PUBLICATIONS

Kato et al. Journal of chemical physics, 2003, 119(21) 11318-11328.*

Burdeniuc, J. et al., "Mineralization of Chlorofluorocarbons and Aromatization of Saturated Fluorocarbons by a Convenient Process", Science, (Jan. 1996), vol. 271, pp. 340-341.

Gething, B. et al., :A New General Route To Aromatic Fluorocarbons, Nature, (Feb. 1959), vol. 183, pp. 588-589.

Harrison, D. et al., :Polycyclic Fluoromatic Compounds -III[1], Octafluoroacenaphthylene, and Decafluoro-indane, -Acenaphthene, -Anthracene, and -Pyrene, Tetrahedron, (1963), vol. 19, pp. 1893-1901.

Hu, C. et al., "Defluorination of Hexadecaflurobicyclo[4,4,0]Dec. 1(6)-Ene: A facile Synthesis of Perfluoroaromtics", J. Fluorine, Chem. (1990), vol. 48, pp. 29-35.

Marsella, J.A. et al., "Selective Reduction of Saturated Perfluorocarbons", J. Org Chem, (1992), vol. 57, No. 10, pp. 2856-2860.

McBee, E.T. et al., "The Preparation of Certain Ethers of Trifluoromethyl-substituted Phenols", J. Am. Chem. Soc., (Apr. 1947), vol. 69, pp. 947-950.

McBee, E.T., et al., "Fluorinated derivatives of mesitylene" Indust. Engng. Chem. (1947), vol. 39, No. 3, pp. 393-394.

Zh. Org. Khim., vol. 7, (1947), pp. 754-751.

Oksenenko, B.G., et al., "Action of Electrophilic Agents on Polyfluoroaromatic Compounds", J. Org. Chem. USSR, pp. 753-758.

Simons, J.H., et al., "Fluorine Derivatives of Acetophenone and Ethylbenzene", J. Am. Chem. Soc., (1943), vol. 65, pp. 2064-2066.

Simons, J.H., et al., "The Preparation of Benzotrifluride", J. Am. Chem. Soc., (1937), vol. 60, pp. 492.

* cited by examiner

*Primary Examiner*—James O. Wilson
*Assistant Examiner*—Yevegeny Valenrod
(74) *Attorney, Agent, or Firm*—Browdy and Neimark, P.L.L.C.

(57) ABSTRACT

Fluorinated pentacene derivatives, for example, the novel compounds tetradecafluoropentacene, 5,6,7,12,13,14-hexafluoropentacene, 5,7,12,14-tetrafluoropentacene, and 6,13-difluoropentacene, and intermediates therefor are provided. And a method of producing fluorinated pentacene derivatives and intermediates therefor is also provided. Pentacene derivatives fluorinated at desired positions of the pentacene skeleton are obtained by introducing the oxo group, hydroxyl group, or alkoxyl group into the pentacene skeleton followed by fluorination with sulfur tetrafluoride and partial defluorination using a reducing agent.

31 Claims, No Drawings

FLUORINATED PENTACENE DERIVATIVE AND METHOD OF PRODUCING SAME

TECHNICAL FIELD

The present invention relates to fluorinated pentacene derivatives and to a method of producing the same. Fluorine-containing pentacene-type compounds are useful compounds that can be employed in a broad range of fields such as organic electronic materials, functional polymer materials, drugs, and agrochemicals and in particular that can be used in these fields as synthesis starting materials.

BACKGROUND ART

Halogen exchange reactions on chlorine-substituted species are known as a method for introducing the fluorine atom into aromatic monocyclic and condensed polycyclic hydrocarbons (scheme 1).

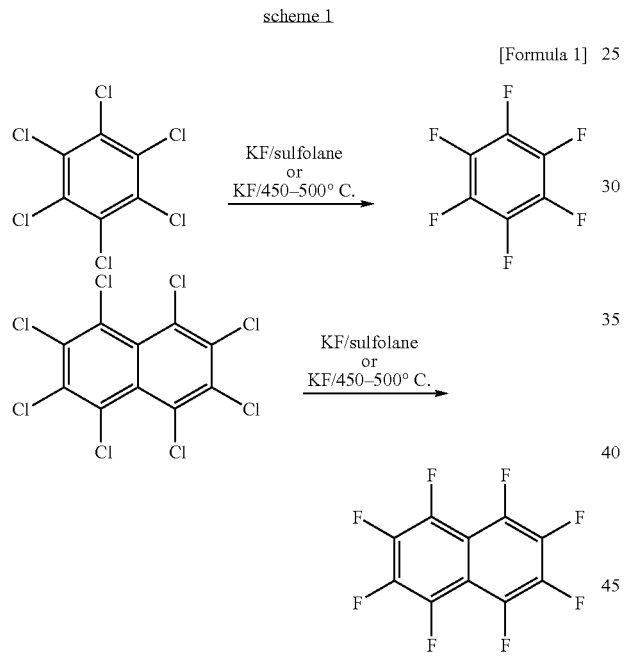

The synthesis of hexafluorobenzene and the synthesis of octafluoronaphthalene, which is useful as a starting material for organic dielectric film materials, by this method has been reported (See Non-patent documents 1 to 3.). A problem with this method, however, is the difficulty in obtaining the starting chlorine-substituted species.

A method has also been reported, as shown in scheme 2, in which a cyclic perfluorocompound is synthesized by a defluorination reaction mediated by reducing agent, such as a metal or the like. For example, hexafluorobenzene (See Non-patent document 4.), octafluoronaphthalene (See Non-patent documents 5 to 7.), and decafluoropyrene (See Non-patent document 8.) have been synthesized by this method. However, very severe reaction conditions, i.e., a reaction temperature of at least 400° C., are generally required when the starting material does not contain a carbon-carbon multiple bond.

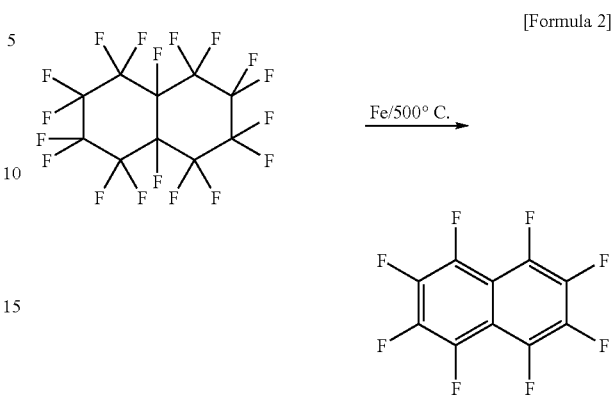

When the starting material has at least one carbon-carbon multiple bond, the defluorination reaction proceeds under mild conditions using metal as the reducing agent. For example, as shown in scheme 3, decafluoroanthracene is obtained from 1,2,3,4,5,6,7,8,9,9,10,10-dodecafluoro-9,10-dihydroanthracene at a reaction temperature of 225-280° C. (See Non-patent document 9.). In addition, octafluoronaphthalene has been obtained by this method from 1,1,2,2,3,3,4,4,5,5,6,6,7,7,8,8-hexadecafluoro-1,2,3,4,5,6,7,8-octahydronaphthalene (See Non-patent document 10.).

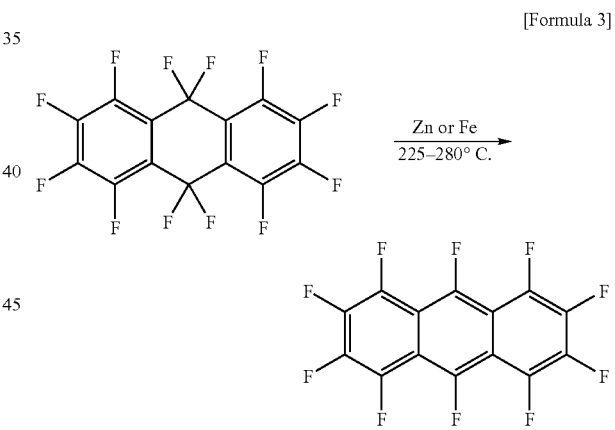

However, it is difficult to obtain fluorinated pentacene derivatives even by the heretofore known methods described above; for example, tetradecafluoropentacene has not been prepared. Moreover, no examples of the synthesis of partially fluorinated pentacene derivatives have been reported.

Non-patent document 1: J. Am. Chem. Soc., 1947, Volume 69, page 947

Non-patent document 2: Indust. Engng. Chem., 1947, Volume 39, page 393

Non-patent document 3: J. Am. Chem. Soc., 1943, Volume 65, page 2064

Non-patent document 4: J. Am. Chem. Soc., 1938, Volume 60, page 492

Non-patent document 5: Nature, 1959, Volume 183, page 588

Non-patent document 6: Science, 1996, Volume 271, page 340

Non-patent document 7: J. Org. Chem., 1992, Volume 57, page 2856

Non-patent document 8: Tetrahedron, 1963, Volume 19, page 1893

Non-patent document 9: Zh. Org. Khim., 1971, Volume 7, page 745

Non-patent document 10: J. Fluorine Chem., 1990, Volume 48, page 29

DISCLOSURE OF THE INVENTION

Problems to be Solved by the Invention

The present invention was achieved in view of the circumstances described above. An object of the present invention is to provide fluorinated pentacene derivatives, for example, the novel compounds tetradecafluoropentacene, 5,6,7,12,13,14-hexafluoropentacene, 5,7,12,14-tetrafluoropentacene, and 6,13-difluoropentacene. An additional object of the present invention is to provide intermediates for the preceding. A further object of the present invention is to provide a method of producing fluorinated pentacene derivatives and intermediates therefor.

Means for Solving the Problems

As a result of focused investigations directed to solving the problems identified above, the inventors discovered that a desired position in the pentacene skeleton can be fluorinated by introducing the oxo group, hydroxyl group, or alkoxyl group into the pentacene skeleton followed by fluorination with sulfur tetrafluoride and partial defluorination using a reducing agent. The present invention was achieved based on this discovery.

More specifically, the gist of the present invention is as follows.

[1] A compound represented by formula [1]

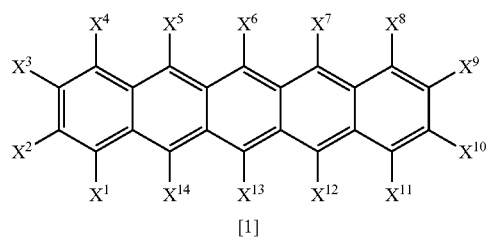

[1]

(wherein $X^1$, $X^2$, $X^3$, $X^4$, $X^5$, $X^6$, $X^7$, $X^8$, $X^9$, $X^{10}$, $X^{11}$, $X^{12}$, $X^{13}$, and $X^{14}$ represent fluorine, hydrogen, a substituted or unsubstituted $C_{1-8}$ alkyl group, a substituted or unsubstituted phenyl group, a substituted or unsubstituted naphthyl group, a substituted or unsubstituted anthracenyl group, a substituted or unsubstituted naphthacenyl group, or a substituted or unsubstituted pentacenyl group, and may be the same or different; or $X^2$ is bonded to $X^3$ to form a monocyclic or condensed polycyclic hydrocarbon group and/or $X^9$ is bonded to $X^{10}$ to form a monocyclic or condensed polycyclic hydrocarbon group)

wherein the groups in at least one pair selected from the group consisting of the pair $X^5$ and $X^{14}$, the pair $X^6$ and $X^{13}$, and the pair $X^7$ and $X^{12}$ are both fluorine.

[2] A compound represented by formula [2]

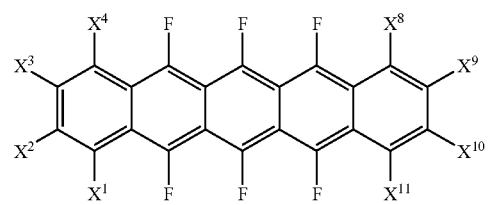

[2]

(wherein $X^1$, $X^2$, $X^3$, $X^4$, $X^8$, $X^9$, $X^{10}$, and $X^{11}$ represent fluorine, hydrogen, a substituted or unsubstituted $C_{1-8}$ alkyl group, a substituted or unsubstituted phenyl group, a substituted or unsubstituted naphthyl group, a substituted or unsubstituted anthracenyl group, a substituted or unsubstituted naphthacenyl group, or a substituted or unsubstituted pentacenyl group, and may be the same or different; or $X^2$ is bonded to $X^3$ to form a monocyclic or condensed polycyclic hydrocarbon group and/or $X^9$ is bonded to $X^{10}$ to form a monocyclic or condensed polycyclic hydrocarbon group).

[3] A compound represented by formula [3]

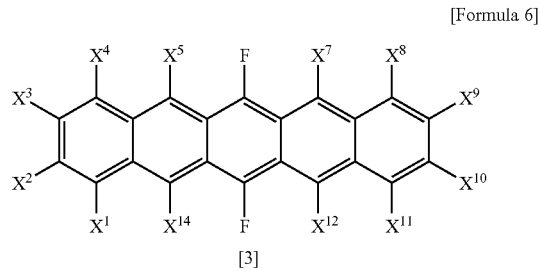

[3]

(wherein $X^1$, $X^2$, $X^3$, $X^4$, $X^5$, $X^7$, $X^8$, $X^9$, $X^{10}$, $X^{11}$, $X^2$, and $X^{14}$ represent fluorine, hydrogen, a substituted or unsubstituted $C_{1-8}$ alkyl group, a substituted or unsubstituted phenyl group, a substituted or unsubstituted naphthyl group, a substituted or unsubstituted anthracenyl group, a substituted or unsubstituted naphthacenyl group, or a substituted or unsubstituted pentacenyl group, and may be the same or different; or $X^2$ is bonded to $X^3$ to form a monocyclic or condensed polycyclic hydrocarbon group and/or $X^9$ is bonded to $X^{10}$ to form a monocyclic or condensed polycyclic hydrocarbon group).

[4] A compound represented by formula [4]

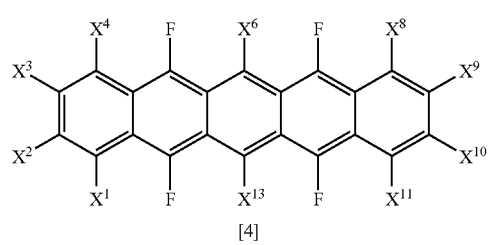

[4]

(wherein $X^1$, $X^2$, $X^3$, $X^4$, $X^6$, $X^8$, $X^9$, $X^{10}$, $X^{11}$, and $X^{12}$ represent fluorine, hydrogen, a substituted or unsubstituted $C_{1-8}$ alkyl group, a substituted or unsubstituted phenyl group, a substituted or unsubstituted naphthyl group, a substituted or unsubstituted anthracenyl group, a substituted or unsubstituted naphthacenyl group, or a substituted or unsubstituted pentacenyl group, and may be the same or different; or $X^2$ is bonded to $X^3$ to form a monocyclic or condensed polycyclic hydrocarbon group and/or $X^9$ is bonded to $X^{10}$ to form a monocyclic or condensed polycyclic hydrocarbon group).

[5] A method of producing a compound represented by formula [13]

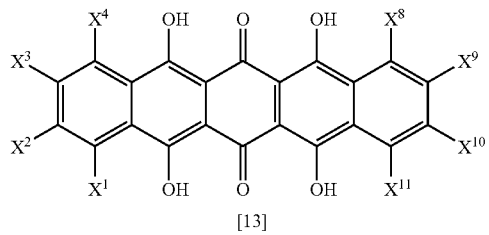

[Formula 10]

[13]

(wherein $X^1$, $X^2$, $X^3$, $X^4$, $X^8$, $X^9$, $X^{10}$, and $X^{11}$ represent fluorine, hydrogen, a substituted or unsubstituted $C_{1-8}$ alkyl group, a substituted or unsubstituted phenyl group, a substituted or unsubstituted naphthyl group, a substituted or unsubstituted anthracenyl group, a substituted or unsubstituted naphthacenyl group, or a substituted or unsubstituted pentacenyl group, and may be the same or different; or $X^2$ is bonded to $X^3$ to form a monocyclic or condensed polycyclic hydrocarbon group and/or $X^9$ is bonded to $X^{10}$ to form a monocyclic or condensed polycyclic hydrocarbon group), comprising the step of producing a compound represented by formula [13] by reacting a compound represented by formula [11]

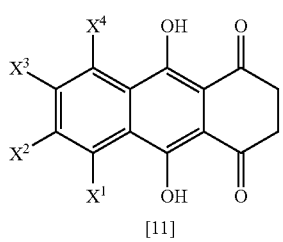

[Formula 8]

[11]

(wherein $X^1$, $X^2$, $X^3$, and $X^4$ represent fluorine, hydrogen, a substituted or unsubstituted $C_{1-8}$ alkyl group, a substituted or unsubstituted phenyl group, a substituted or unsubstituted naphthyl group, a substituted or unsubstituted anthracenyl group, a substituted or unsubstituted naphthacenyl group, or a substituted or unsubstituted pentacenyl group, and may be the same or different; or $X^2$ is bonded to $X^3$ to form a monocyclic or condensed polycyclic hydrocarbon group) with a compound represented by formula [12]

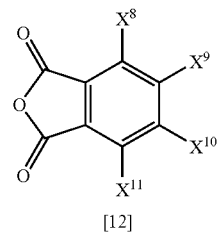

[Formula 9]

[12]

(wherein $X^8$, $X^9$, $X^{10}$, and $X^{11}$ represent fluorine, hydrogen, a substituted or unsubstituted $C_{1-8}$ alkyl group, a substituted or unsubstituted phenyl group, a substituted or unsubstituted naphthyl group, a substituted or unsubstituted anthracenyl group, a substituted or unsubstituted naphthacenyl group, or a substituted or unsubstituted pentacenyl group, and may be the same or different; or $X^9$ is bonded to $X^{10}$ to form a monocyclic or condensed polycyclic hydrocarbon group) in the presence of a Lewis acid.

[6] The production method according to [5], wherein the Lewis acid comprises aluminum chloride.

[7] A method of producing a compound represented by formula [14]

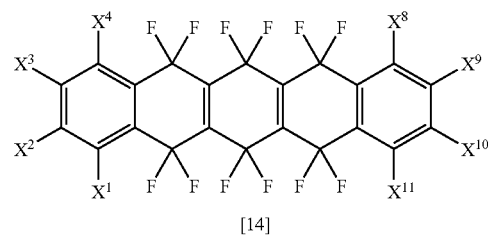

[Formula 11]

[14]

(wherein $X^1$, $X^2$, $X^3$, $X^4$, $X^8$, $X^9$, $X^{10}$, and $X^{11}$ are defined as for formula [13]), comprising the step of producing a compound represented by formula [14] by reacting a compound represented by formula [13] with a fluorinating agent.

[8] A method of producing a compound represented by formula [15]

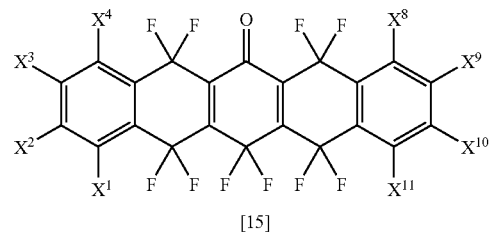

[Formula 12]

[15]

(wherein $X^1, X^2, X^3, X^4, X^8, X^9, X^{10}$, and $X^{11}$ are defined as for formula [13]), comprising the step of
producing a compound represented by formula [15] by reacting a compound represented by formula [13] with a fluorinating agent.

[9] A method of producing a compound represented by formula [14], comprising the step of
producing a compound represented by formula [14] by reacting a compound represented by formula [15] with a fluorinating agent.

[10] A method of producing a compound represented by formula [16]

[Formula 13]

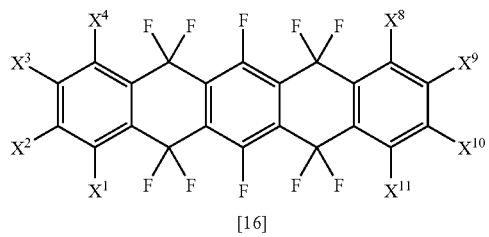

[16]

(wherein $X^1, X^2, X^3, X^4, X^8, X^9, X^{10}$, and $X^{11}$ are defined as for formula [13]), comprising the step of
producing a compound represented by formula [16] by reacting a compound represented by formula [13] with a fluorinating agent.

[11] The production method according to any of [7] to [10], wherein the fluorinating agent comprises sulfur tetrafluoride.

[12] A method of producing a compound represented by formula [2], comprising the step of
producing a compound represented by formula [2] by reacting a compound represented by formula [14] with a reducing agent.

[13] A method of producing a compound represented by formula [2], comprising the step of
producing a compound represented by formula [2] by reacting a compound represented by formula [16] with a reducing agent.

[14] The production method according to [12] or [13], wherein the reducing agent comprises zinc, iron, copper, nickel, palladium, or a combination thereof.

[15] A compound represented by formula [13].
[16] A compound represented by formula [14].
[17] A compound represented by formula [15].
[18] A compound represented by formula [16].
[19] A method of producing a compound represented by formula [22]

[Formula 15]

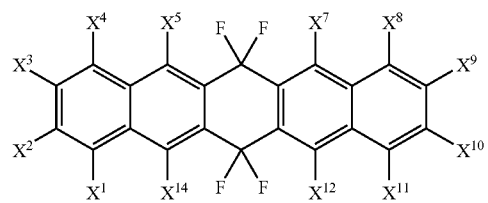

[22]

(wherein $X^1, X^2, X^3, X^4, X^5, X^7, X^8, X^9, X^{10}, X^{11}, X^{12}$, and $X^{14}$ are defined as for formula [21]), comprising the step of
producing a compound represented by formula [22] by reacting a compound represented by formula [21]

[Formula 14]

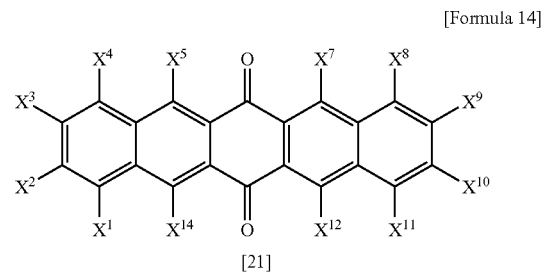

[21]

(wherein $X^1, X^2, X^3, X^4, X^5, X^7, X^8, X^9, X^{10}, X^{11}, X^{12}$, and $X^{14}$ represent fluorine, hydrogen, a substituted or unsubstituted $C_{1-8}$ alkyl group, a substituted or unsubstituted phenyl group, a substituted or unsubstituted naphthyl group, a substituted or unsubstituted anthracenyl group, a substituted or unsubstituted naphthacenyl group, or a substituted or unsubstituted pentacenyl group, and may be the same or different; or $X^2$ is bonded to $X^3$ to form a monocyclic or condensed polycyclic hydrocarbon group and/or $X^9$ is bonded to $X^{10}$ to form a monocyclic or condensed polycyclic hydrocarbon group) with a fluorinating agent.

[20] A method of producing a compound represented by formula [23]

[Formula 16]

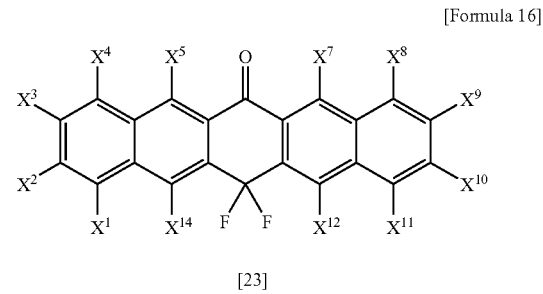

[23]

(wherein $X^1, X^2, X^3, X^4, X^5, X^7, X^8, X^9, X^{10}, X^{11}, X^{12}$, and $X^{14}$ are defined as for formula [21]), comprising the step of
producing a compound represented by formula [23] by reacting a compound represented by formula [21] with a reducing agent.

[21] A method of producing a compound represented by formula [22], comprising the step of
producing a compound represented by formula [22] by reacting a compound represented by formula [23] with a fluorinating agent.

[22] The production method according to any of [19] to [21], wherein the fluorinating agent comprises sulfur tetrafluoride.

[23] A method of producing a compound represented by formula [3], comprising the step of
producing a compound represented by formula [3] by reacting a compound represented by formula [22] with a fluorinating agent.

[24] The production method according to [23], wherein the reducing agent comprises zinc, iron, copper, nickel, palladium, or a combination thereof.

[25] A compound represented by formula [22].

[26] A compound represented by formula [23].

[27] A method of producing a compound represented by formula [32]

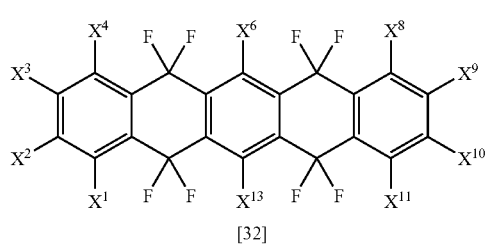

[32]

(wherein $X^1$, $X^2$, $X^3$, $X^4$, $X^6$, $X^8$, $X^9$, $X^{10}$, $X^{11}$, and $X^{13}$ are defined as for formula [31]), comprising the step of producing a compound represented by formula [32] by reacting a compound represented by formula [31]

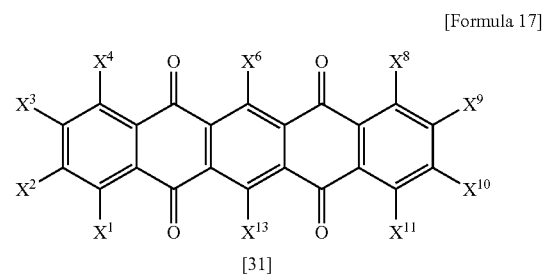

[31]

(wherein $X^1$, $X^2$, $X^3$, $X^4$, $X^6$, $X^8$, $X^9$, $X^{10}$, $X^{11}$, and $X^{13}$ represent fluorine, hydrogen, a substituted or unsubstituted $C_{1-8}$ alkyl group, a substituted or unsubstituted phenyl group, a substituted or unsubstituted naphthyl group, a substituted or unsubstituted anthracenyl group, a substituted or unsubstituted naphthacenyl group, or a substituted or unsubstituted pentacenyl group, and may be the same or different; or $X^2$ is bonded to $X^3$ to form a monocyclic or condensed polycyclic hydrocarbon group and/or $X^9$ is bonded to $X^{10}$ to form a monocyclic or condensed polycyclic hydrocarbon group) with a fluorinating agent.

[28] A method of producing a compound represented by formula [33]

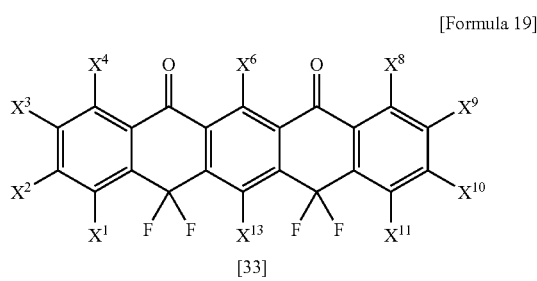

[33]

(wherein $X^1$, $X^2$, $X^3$, $X^4$, $X^6$, $X^8$, $X^9$, $X^{10}$, $X^{11}$, and $X^{13}$ are defined as for formula [31]), comprising the step of producing a compound represented by formula [33] by reacting a compound represented by formula [31] with a fluorinating agent.

[29] A method of producing a compound represented by formula [32], comprising the step of producing a compound represented by formula [32] by reacting a compound represented by formula [33] with a fluorinating agent.

[30] The production method according to any of [27] to [29], wherein the fluorinating agent comprises sulfur tetrafluoride.

[31] A method of producing a compound represented by formula [4], comprising the step of producing a compound represented by formula [4] by reacting a compound represented by formula [32] with a reducing agent.

[32] The production method according to [31], wherein the reducing agent comprises zinc, iron, copper, nickel, palladium, or a combination thereof.

[33] A compound represented by formula [31].

[34] A compound represented by formula [32].

BEST MODE FOR CARRYING OUT THE INVENTION

The present invention enables the synthesis of fluorinated pentacene derivatives by enabling the positionally selective introduction of the fluorine group into the pentacene skeleton. Here, the pentacene skeleton denotes a skeleton in which at least five 6-membered carbon rings are condensed. Fluorinated pentacene derivative denotes a compound in which at least one of the carbon atoms that form the pentacene skeleton is bonded to fluorine. A partially fluorinated pentacene derivative denotes a compound in which at least one of the carbon atoms that form the pentacene skeleton is bonded to fluorine and at least one of the carbon atoms that form the pentacene skeleton is not bonded to fluorine.

In order to bond the fluorine group in the pentacene skeleton, an oxygen functional group is first bonded to the carbon atom at a desired position. Here, oxygen functional group denotes a functional group that forms a bond through an oxygen atom with a carbon atom that forms the pentacene skeleton, and comprises the oxo group, hydroxyl group, and alkoxyl group. Then, through a fluorination reaction, the oxygen functional group is removed from the carbon atom and two fluorine groups become bonded to the one carbon atom thereinstead. A partial defluorination reaction then removes one fluorine group from the one carbon atom.

Fluorinated pentacene derivatives synthesized by the present invention are compounds represented by formula [1]

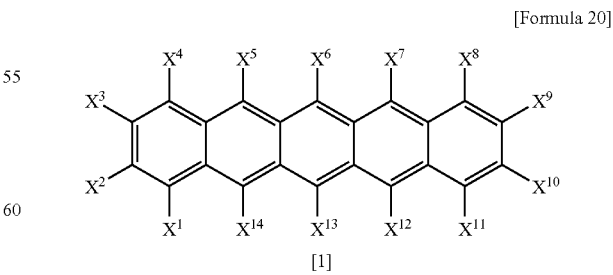

[1]

(wherein $X^1$, $X^2$, $X^3$, $X^4$, $X^5$, $X^6$, $X^7$, $X^8$, $X^9$, $X^{10}$, $X^{11}$, $X^{12}$, $X^{13}$, and $X^{14}$ represent fluorine, hydrogen, a substituted or unsubstituted $C_{1-8}$ alkyl group, a substituted or unsubstituted phenyl group, a substituted or unsubstituted naphthyl group, a substituted or unsubstituted anthracenyl group, a substituted or unsubstituted naphthacenyl group, or a substituted or unsubstituted pentacenyl group, and may be the same or different; or $X^2$ is bonded to $X^3$ to form a monocyclic or condensed polycyclic hydrocarbon group and/or $X^9$ is bonded to $X^{10}$ to form a monocyclic or condensed polycyclic hydrocarbon group) wherein the groups in at least one pair selected from the group consisting of the pair $X^5$ and $X^{14}$, the pair $X^6$ and $X^{13}$, and the pair $X^7$ and $X^{12}$ are both fluorine. Compounds with formula [1] encompass compounds with formula [2]

[Formula 21]

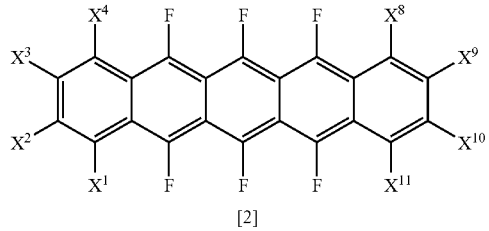

[2]

(wherein $X^1$, $X^2$, $X^3$, $X^4$, $X^8$, $X^9$, $X^{10}$, and $X^{11}$ represent fluorine, hydrogen, a substituted or unsubstituted $C_{1-8}$ alkyl group, a substituted or unsubstituted phenyl group, a substituted or unsubstituted naphthyl group, a substituted or unsubstituted anthracenyl group, a substituted or unsubstituted naphthacenyl group, or a substituted or unsubstituted pentacenyl group, and may be the same or different; or $X^2$ is bonded to $X^3$ to form a monocyclic or condensed polycyclic hydrocarbon group and/or $X^9$ is bonded to $X^{10}$ to form a monocyclic or condensed polycyclic hydrocarbon group); compounds with formula [3]

[Formula 22]

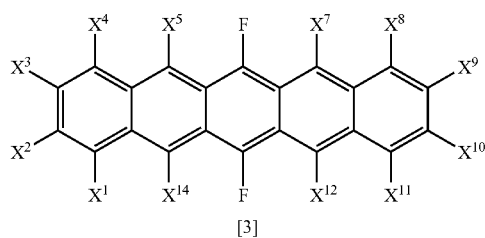

[3]

(wherein $X^1$, $X^2$, $X^3$, $X^4$, $X^5$, $X^7$, $X^8$, $X^9$, $X^{10}$, $X^{11}$, $X^{12}$, and $X^{14}$ represent fluorine, hydrogen, a substituted or unsubstituted $C_{1-8}$ alkyl group, a substituted or unsubstituted phenyl group, a substituted or unsubstituted naphthyl group, a substituted or unsubstituted anthracenyl group, a substituted or unsubstituted naphthacenyl group, or a substituted or unsubstituted pentacenyl group, and may be the same or different; or $X^2$ is bonded to $X^3$ to form a monocyclic or condensed polycyclic hydrocarbon group and/or $X^9$ is bonded to $X^{10}$ to form a monocyclic or condensed polycyclic hydrocarbon group); and formula [4]

[Formula 23]

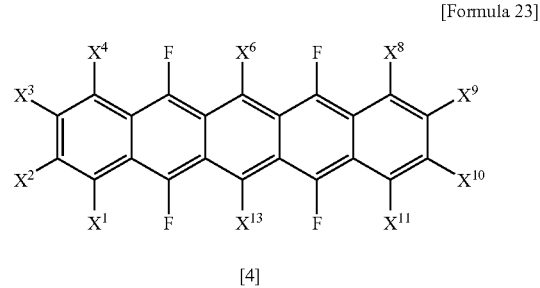

[4]

(wherein $X^1$, $X^2$, $X^3$, $X^4$, $X^6$, $X^8$, $X^9$, $X^{10}$, $X^{11}$, and $X^{13}$ represent fluorine, hydrogen, a substituted or unsubstituted $C_{1-8}$ alkyl group, a substituted or unsubstituted phenyl group, a substituted or unsubstituted naphthyl group, a substituted or unsubstituted anthracenyl group, a substituted or unsubstituted naphthacenyl group, or a substituted or unsubstituted pentacenyl group, and may be the same or different; or $X^2$ is bonded to $X^3$ to form a monocyclic or condensed polycyclic hydrocarbon group and/or $X^9$ is bonded to $X^{10}$ to form a monocyclic or condensed polycyclic hydrocarbon group).

$X^2$ and $X^3$ in the preceding formulas may be bonded to each other to form a saturated or unsaturated monocyclic or condensed polycyclic hydrocarbon group. $X^9$ and $X^{10}$ in the preceding formulas may also be bonded to each other to form a saturated or unsaturated monocyclic or condensed polycyclic hydrocarbon group. This monocyclic hydrocarbon group also encompasses groups in which monocyclic hydrocarbon groups are connected to each other by a carbon-carbon single bond. The monocyclic hydrocarbon groups encompass monocyclic aromatic rings and the condensed polycyclic hydrocarbon groups encompass condensed polycyclic aromatic rings. The aromatic rings can be exemplified by the benzene ring, naphthalene ring, and anthracene ring, but are not limited thereto. The monocyclic hydrocarbon group and condensed polycyclic hydrocarbon group may in each case be substituted or unsubstituted. $X^1$, $X^4$, $X^5$, $X^6$, $X^7$, $X^8$, $X^{11}$, $X^{12}$, $X^{13}$, and $X^{14}$ are defined as above even when $X^2$ and $X^3$ are bonded to each other to form a saturated or unsaturated monocyclic or condensed polycyclic hydrocarbon group and/or $X^9$ and $X^{10}$ are bonded to each other to form a saturated or unsaturated monocyclic or condensed polycyclic hydrocarbon group.

The substituted alkyl groups encompass fluoroalkyl groups. Here, fluoroalkyl denotes a group in which at least one of the hydrogen atoms in an alkyl group is replaced by the fluorine atom, and further substitution by other substituents may be present. The fluoroalkyl group encompasses perfluoroalkyl groups.

The substituted phenyl groups encompass fluorophenyl groups. Here, fluorophenyl denotes a group in which at least one of the hydrogen atoms in the phenyl group is replaced by the fluorine atom, and further substitution by other substituents may be present. The fluorophenyl group encompasses the pentafluorophenyl group.

The substituted naphthyl groups encompass fluoronaphthyl groups. Here, fluoronaphthyl denotes a group in which at least one of the hydrogen atoms in the naphthyl group is replaced by the fluorine atom, and further substitution by other substituents may be present. The fluoronaphthyl group encompasses the heptafluoronaphthyl group.

The substituted anthranyl groups encompass fluoroanthranyl groups. Here, fluoroanthranyl denotes a group in which at least one of the hydrogen atoms in the anthranyl group is replaced by the fluorine atom, and further substitution by other substituents may be present. The fluoroanthranyl group encompasses the nonafluoroanthranyl group.

The substituted naphthacenyl groups encompass fluoronaphthacenyl groups. Here, fluoronaphthacenyl denotes a group in which at least one of the hydrogen atoms in the naphthacenyl group is replaced by the fluorine atom, and further substitution by other substituents may be present. The fluoronaphthacenyl group encompasses the undecafluoronaphthacenyl group.

The substituted pentacenyl groups encompass fluoropentacenyl groups. Here, fluoropentacenyl denotes a group in which at least one of the hydrogen atoms in the pentacenyl group is replaced by the fluorine atom, and further substitution by other substituents may be present. The fluoropentacenyl group encompasses the tridecafluoropentacenyl group.

The method for producing a compound with formula [2] will be described hereinbelow.

A compound with formula [13] is first obtained by reacting a compound with formula [11] with a compound with formula [12] in the presence of a Lewis acid. The combination of a Lewis acid with sodium chloride may also be used.

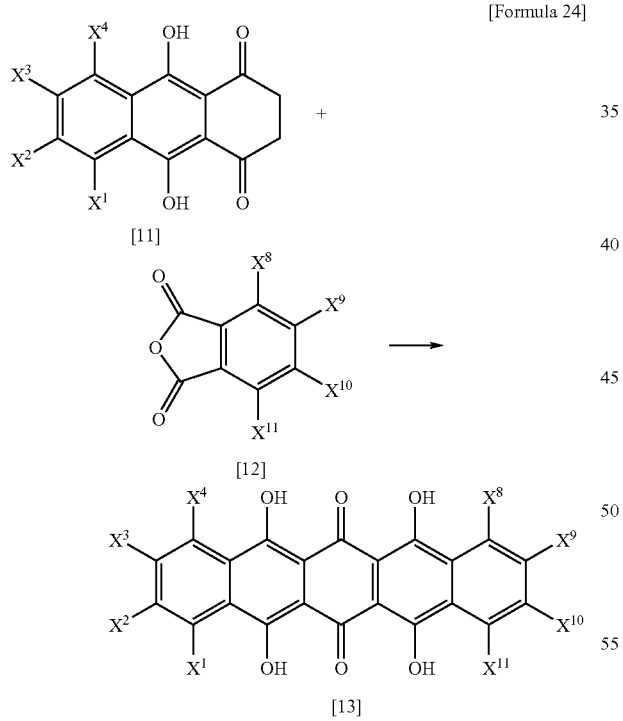

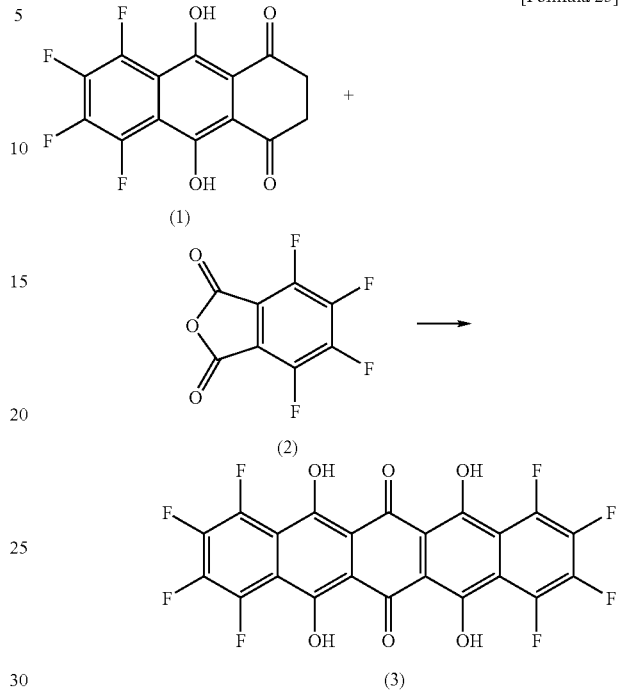

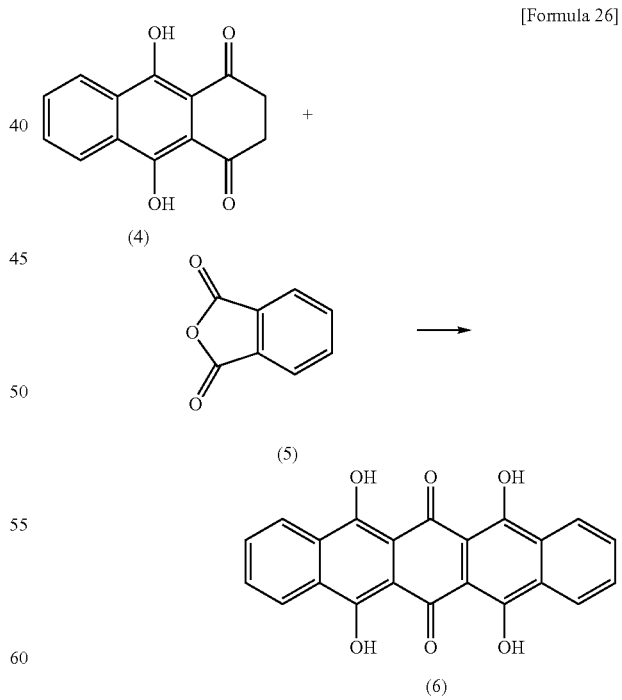

For example, 5,6,7,8-tetrafluoro-9,10-dihydroxy-2,3-dihydroanthracen-1,4-dione (1) is reacted with 4,5,6,7-tetrafluoroisobenzofuran-1,3-dione (2) to give 1,2,3,4,8,9,10,11-octafluoro-5,7,12,14-tetrahydroxypentacen-6,13-dione (3) (scheme 5). In addition, 5,7,12,14-tetrahydroxypentacen-6,13-dione (6) can be obtained from 9,10-dihydroxy-2,3-dihydroanthracen-1,4-dione (4) and isobenzofuran-1,3-dione (5) (scheme 6).

The Lewis acid used in scheme 4 is not particularly limited, but, for example, aluminum chloride, zinc chloride, iron (III) chloride, tin (IV) chloride, or boron trifluoride ether complex can be used, among which aluminum chloride is preferred.

The Lewis acid is used at 0.1 to 5.0 equivalents with reference to the starting material and is preferably used at 0.2 to 1.0 equivalent with reference to the starting material.

When sodium chloride is used along with the Lewis acid, the former is used at 0.1 to 10.0 equivalents with reference to the starting material and preferably at 5.0 to 7.0 equivalents with reference to the starting material.

The compound with formula [12] is used at 1.0 to 5.0 equivalents and preferably 1.1 to 2.0 equivalents with reference to the compound with formula [11]. The reaction temperature is 0 to 320° C. and preferably 200 to 300° C. The reaction time is preferably 1 to 10 hours. After the completion of the reaction, the target compound is obtained by execution of the usual work-up and then purification.

The compound with formula [13] is then fluorinated by reaction with a fluorinating agent.

In one embodiment, a compound with formula [14] is obtained by reacting a compound with formula [13] with a fluorinating agent. A compound with formula [15] may also be produced in this reaction in addition to the compound with formula [14]. The compound with formula [15] can be converted into the compound with formula [14] by further reaction with fluorinating agent.

scheme 7

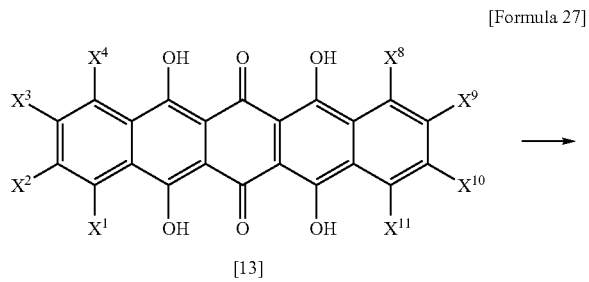

[Formula 27]

scheme 8

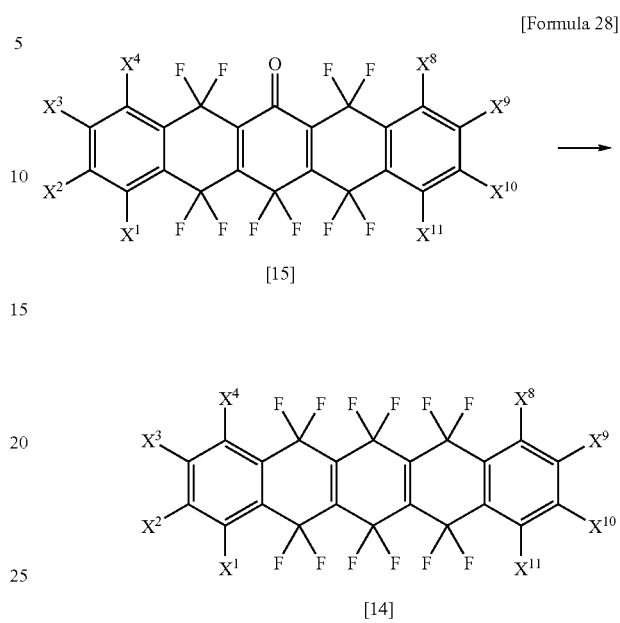

[Formula 28]

For example, 1,2,3,4,5,5,6,6,7,7,8,9,10,11,12,12,13,13,14,14-eicosafluoro-5,6,7,12,13,14-hexahydropentacene (7) and 1,2,3,4,5,5,7,7,8,9,10,11,12,12,14,14-hexadecafluoro-5,7,12,14-tetrahydropentacen-6,13-dione (17) are obtained by reacting 1,2,3,4,8,9,10,11-octafluoro-5,7,12,14-tetrahydroxypentacen-6,13-dione (3) with sulfur tetrafluoride (scheme 9). (7) is obtained by further scheme 9

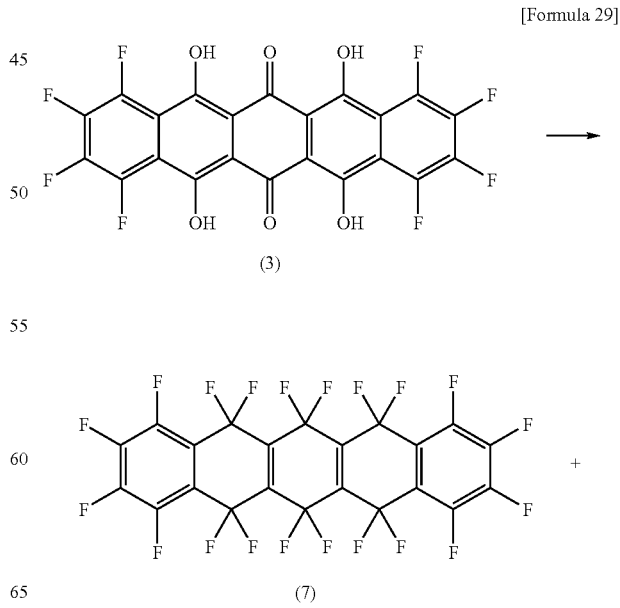

[Formula 29]

-continued

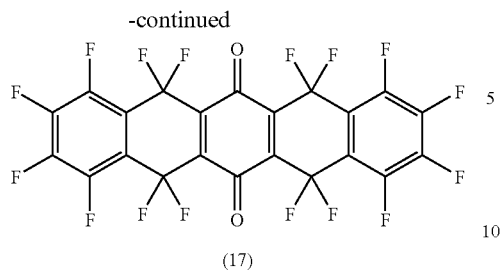
(17)

scheme 10

[Formula 30]
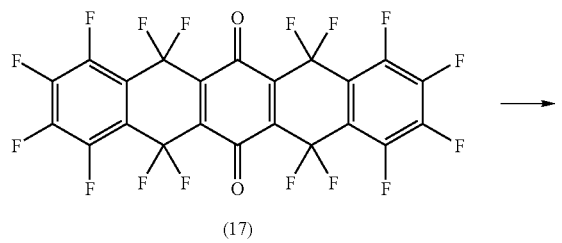
(17)

→

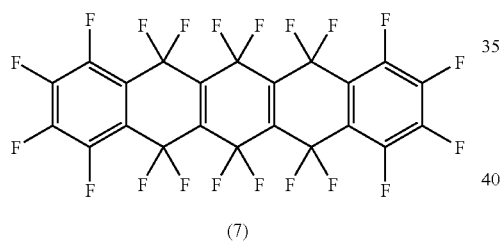
(7)

In a separate embodiment, a compound with formula [16] is obtained by reacting a compound with formula [13] with fluorinating agent.

scheme 11

[Formula 31]
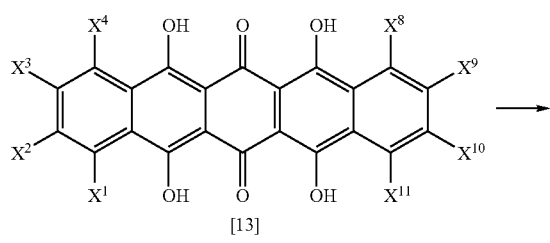
[13]

-continued

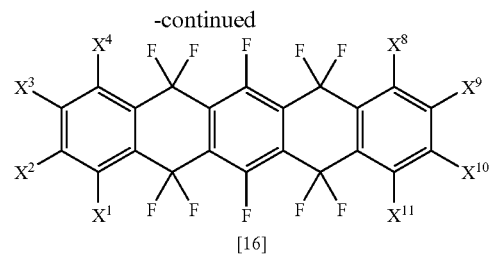
[16]

For example, 5,5,6,7,7,12,12,13,14,14-decafluoro-5,7,12,14-tetrahydropentacene (8) is obtained by reacting 5,7,12,14-tetrahydroxypentacen-6,13-dione (6) with a fluorinating agent.

scheme 12

[Formula 32]
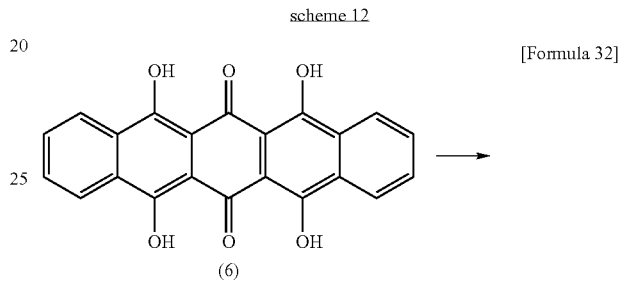
(6)

→

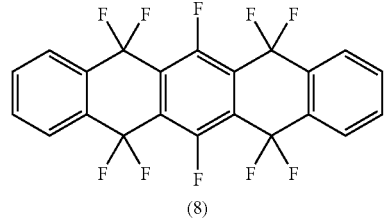
(8)

A compound with formula [2] is obtained by reacting the compound with formula [14] or [16] with a reducing agent.

scheme 13

[Formula 33]
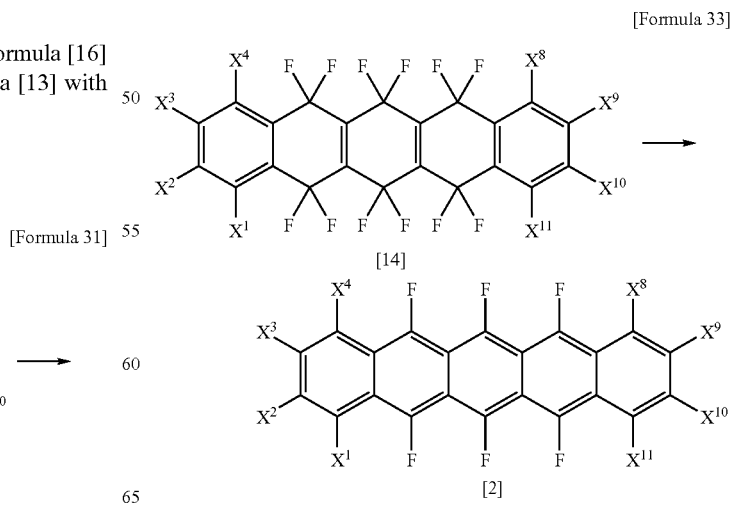
[14]

→

[2]

scheme 14

[Formula 34]

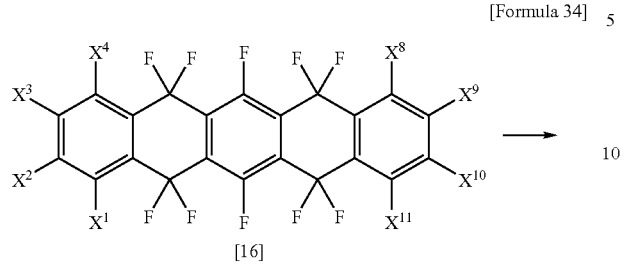

[16]

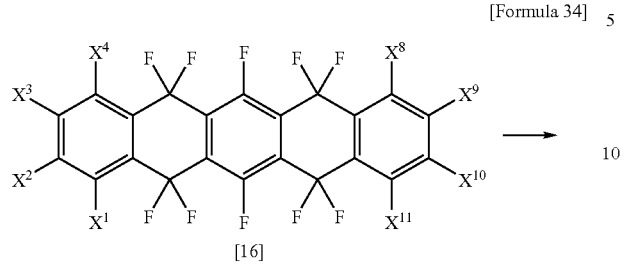

[2]

For example, tetradecafluoropentacene (9) is obtained by reacting 1,2,3,4,5,5,6,6,7,7,8,9,10,11,12,12,13,13,14,14-eicosafluoro-5,6,7,12,13,14-hexahydropentacene (7) with a reducing agent (scheme 15). In addition, 5,6,7,12,13,14-hexafluoropentacene (10) is obtained by reacting 5,5,6,7,7,12,12,13,14,14-decafluoro-5,7,12,14-tetrahydropentacene (8) with a reducing agent (scheme 16).

scheme 15

[Formula 35]

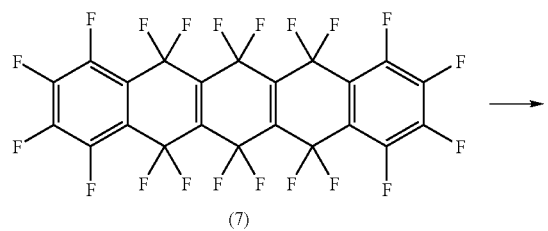

(7)

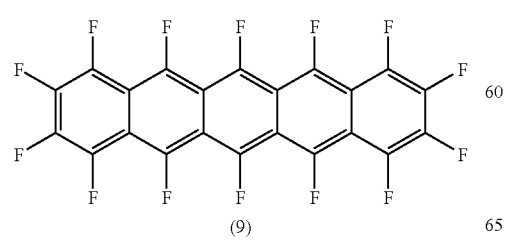

(9)

scheme 16

[Formula 36]

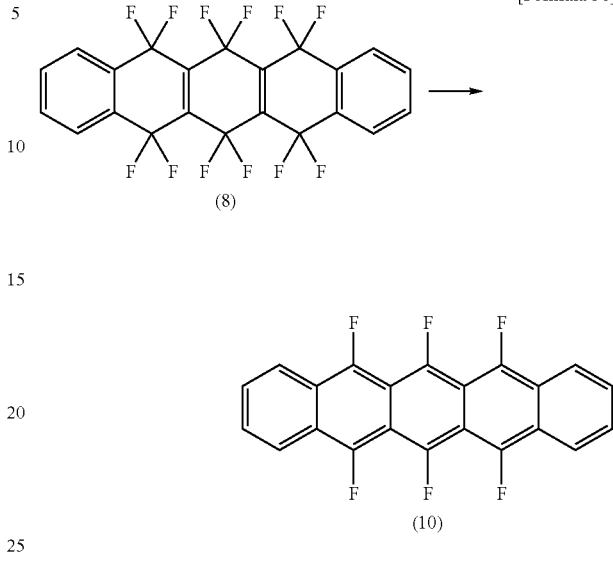

The method for producing a compound with formula [3] is described hereinbelow.

First, a compound with formula [22] is obtained by reacting a compound with formula [21] with a fluorinating agent. A compound with formula [23] may also be produced in this reaction in addition to the compound with formula [22]. This compound with formula [23] can be converted into a compound with formula [22] by further reaction with a fluorinating agent.

scheme 17

[Formula 37]

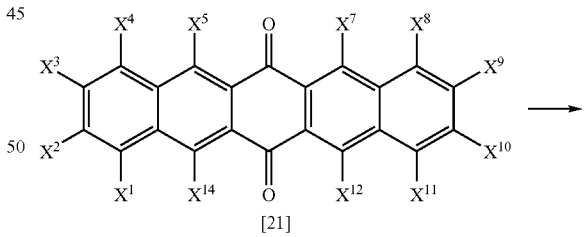

[21]

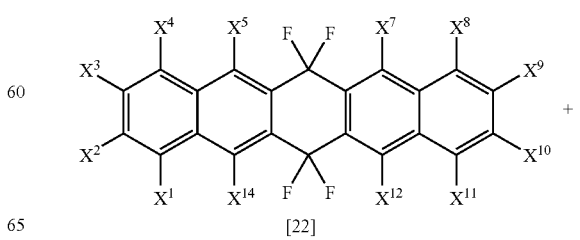

[22]

scheme 18

[Formula 38]

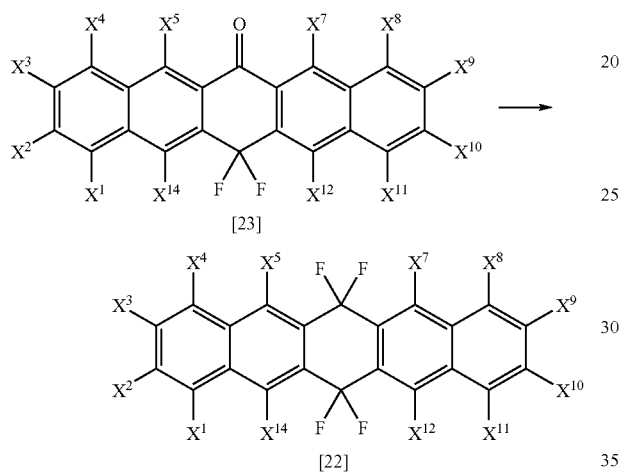

A compound with formula [3] is obtained by reacting the compound with formula [22] with a reducing agent.

scheme 19

[Formula 39]

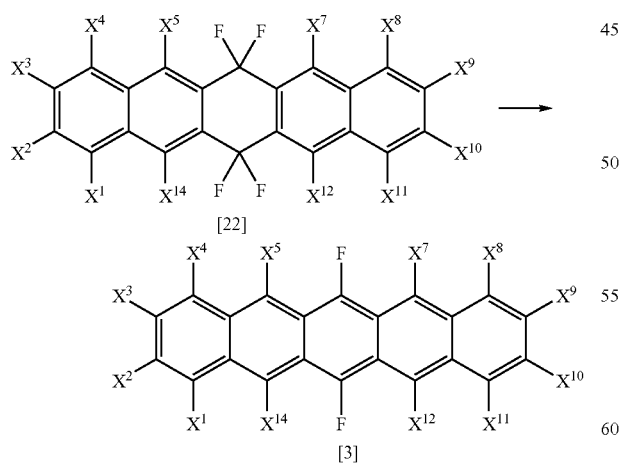

For example, 6,6,13,13-tetrafluoropentacene (15) and 13,13-difluoro-13H-pentacen-6-one (19) are obtained by reacting pentacen-6,13-dione (14) with a fluorinating agent (scheme 20). (15) is obtained by further reaction of (19) with fluorinating agent (scheme 21). 6,13-difluoropentacene (16) is then obtained by reacting (15) with reducing agent (scheme 22).

scheme 20

[Formula 40]

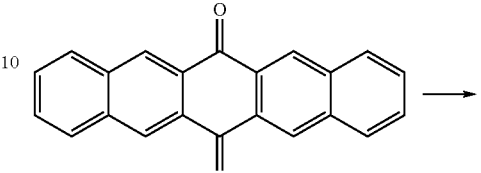

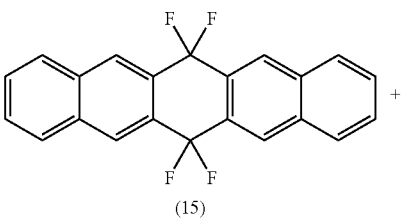

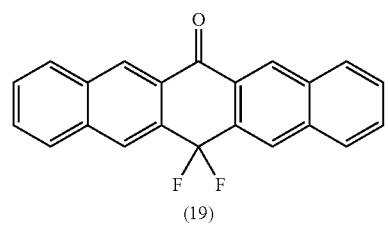

scheme 21

[Formula 41]

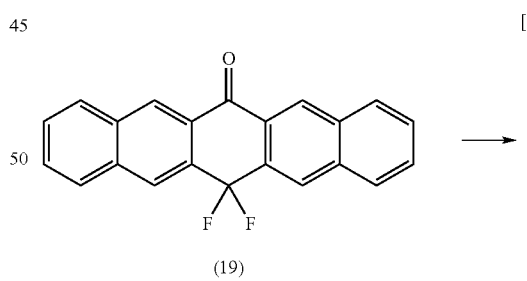

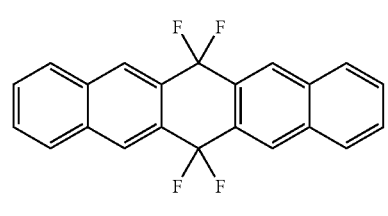

scheme 22

[Formula 42]

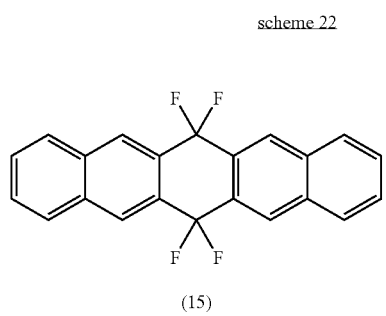

(15)

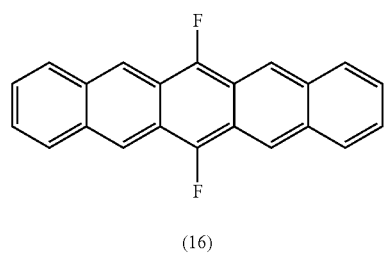

(16)

Pentacen-6,13-dione (14) can be acquired as a commercial product; for example, it can be acquired from the Aldrich Co.

The method for producing a compound with formula (4) is described in the following.

First, a compound with formula [32] is obtained by reacting a compound with formula [31] with a fluorinating agent. A compound with formula [33] may also be produced in this reaction. This compound with formula [33] can be converted into a compound with formula [32] by further reaction with a fluorinating agent.

scheme 23

[Formula 43]

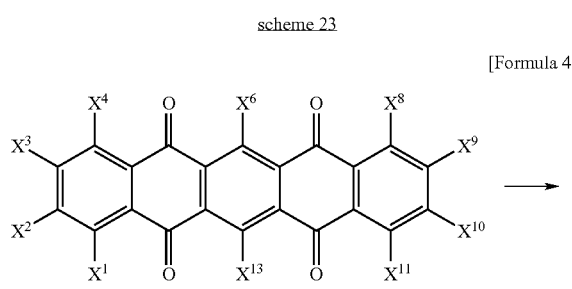

[31]

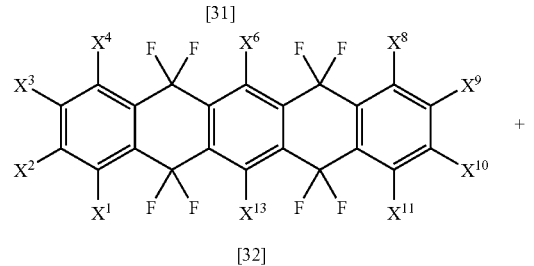

[32]

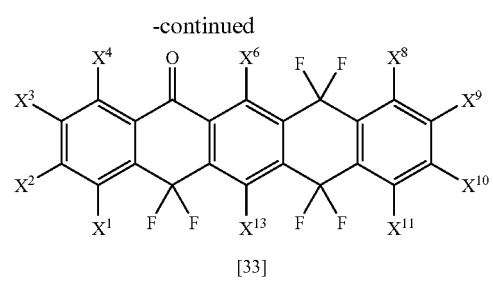

[33]

scheme 24

[Formula 44]

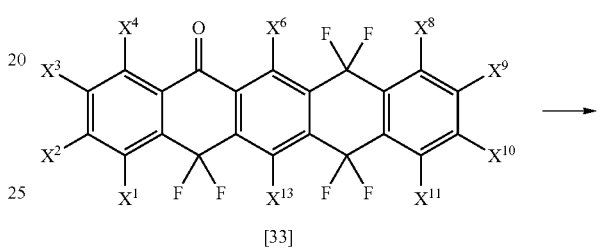

[33]

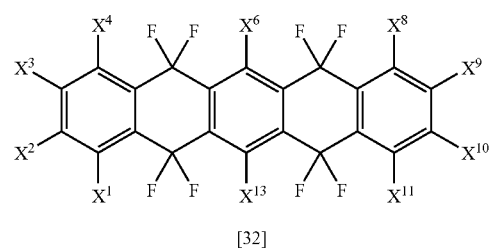

[32]

A compound with formula [4] is obtained by reacting the compound with formula [32] with a reducing agent.

scheme 25

[Formula 45]

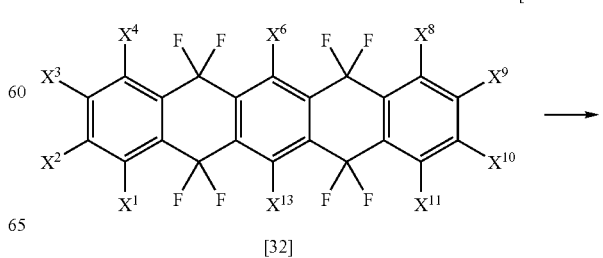

[32]

-continued

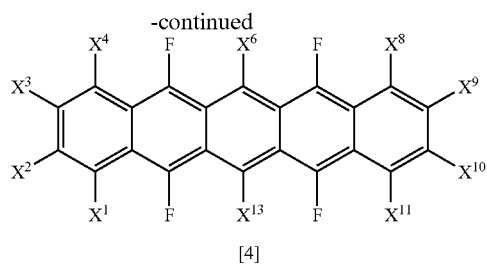

[4]

For example, 5,5,7,7,12,12,14,14-octafluoro-5,7,12,14-tetrahydropentacene (12) and 7,7,12,12,14,14-hexafluoro-7,14-dihydro-12H-pentacen-5-one (18) are obtained by reacting pentacen-5,7,12,14-tetraone (11) with a fluorinating agent (scheme 26). (12) is obtained by the further reaction of (18) with fluorinating agent (scheme 27). 5,7,12,14-tetrafluoropentacene (13) is obtained by reacting (12) with a reducing agent (scheme 28).

scheme 26

[Formula 46]

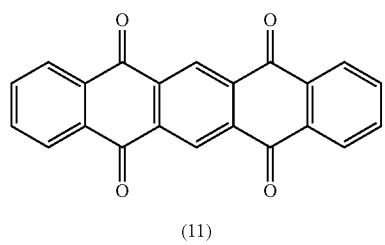

(11)

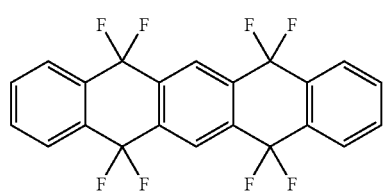

(12)

+

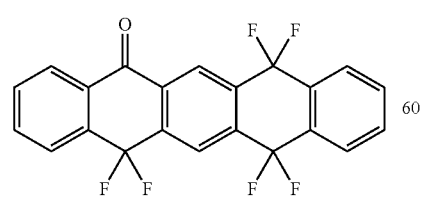

(18)

scheme 27

[Formula 47]

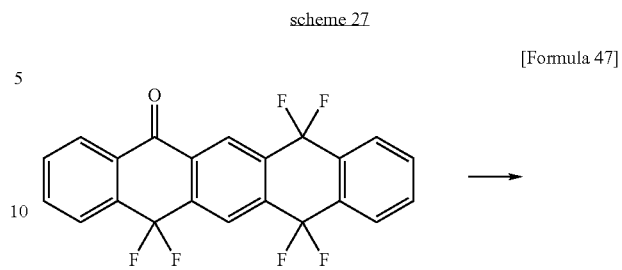

(18)

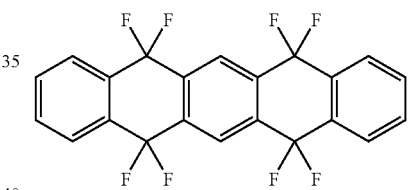

(12)

scheme 28

[Formula 48]

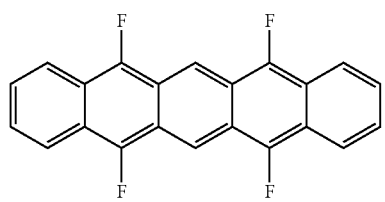

(12)

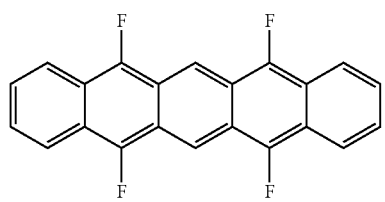

(13)

Pentacen-5,7,12,14-tetraone (11) can be acquired as a commercial product; for example, it can be acquired from the Avocado Co.

During the production sequence for the aforementioned compounds with formulas [2] to [4], compounds may be formed, other than and in addition to the compounds with formulas [15], [23], and [33], in which an oxo group remains present in the absence of fluorination. These compounds can be further reacted with fluorinating agent to remove the oxo group and effect fluorination.

The fluorination step in schemes 7 to 12, 17, 18, 20, 21, 23, 24, 26, and 27 is described hereinbelow.

There are no particular limitations on the fluorinating agent and a variety of fluorides can be used; however, Group 15 and Group 16 fluorides are preferred and sulfur tetrafluoride is more preferred. The preferred quantity of use for sulfur tetrafluoride is 4.0-fold to 30.0-fold on a molar basis with respect to the starting material. More preferred quantities of use for sulfur tetrafluoride are 12.0- to 30.0-fold on a molar basis in scheme 9, 12.0- to 30.0-fold on a molar basis in scheme 12, 4.0- to 10.0-fold on a molar basis in scheme 20, 4.0- to 10.0-fold on a molar basis in scheme 21, 8.0- to 20.0-fold on a molar basis in scheme 26, and 4.0- to 10.0-fold on a molar basis in scheme 27.

A single fluorinating agent or a combination of fluorinating agents may be used. For example, a mixture of sulfur tetrafluoride and hydrogen fluoride can be used. When the reaction is carried out under pressure, hydrogen fluoride can also function as a solvent.

Only starting material and fluorinating agent may be used in the fluorination step; however, other substances may also be present. These co-present substances can function as solvent or catalyst. There are no particular limitations on substances that act as a solvent as long as the substance is a liquid under the reaction conditions. Examples here are the hydrogen fluoride already mentioned above and chlorinated solvents such as dichloromethane and chloroform. A single solvent or a combination of solvents can be used. When hydrogen fluoride is used, it is preferably used at 1 to 20 mL per 1 g starting material.

The fluorination step can be carried out at ambient temperature, but is preferably carried out under pressure in those cases in which heating is employed. Preferred conditions are a reaction pressure of 0 to 20 MPa, a reaction temperature of −40° C. to 320° C., and a reaction time of 2 to 150 hours.

After completion of the reaction, the usual work-up is carried out followed by purification to yield the target compound. The heretofore known procedures can be used for purification, including solvent extraction and recrystallization. In the case of scheme 9, for example, solvent extraction can be carried out with an organic solvent such as chloroform, followed by recrystallization to give the target compounds (7) and (17).

The defluorination step in schemes 13 to 16, 19, 22, 25, and 28 is described in the following.

There are no limitations on the reducing agent used in the defluorination step, and reducing agents regarded as generally having a reducing function can be used. The reducing agent can be exemplified by the following: simple substances of Group 1 elements such as lithium, sodium, potassium, rubidium, and cesium; simple substances of Group 2 elements such as beryllium, magnesium, calcium, strontium, and barium; simple substances of Group 3 elements such as scandium, yttrium, and lanthanides; simple substances of Group 4 elements such as titanium, zirconium, and hafnium; simple substances of Group 5 elements such as vanadium, niobium, and tantalum; simple substances of Group 6 elements such as chromium, molybdenum, and tungsten; simple substances of Group 7 elements such as manganese and rhenium; simple substances of Group 8 elements such as iron, ruthenium, and osmium; simple substances of Group 9 elements such as cobalt, rhodium, and iridium; simple substances of Group 10 elements such as nickel, palladium, and platinum; simple substances of Group 11 elements such as copper, silver, and gold; simple substances of Group 12 elements such as zinc, cadmium, and mercury; simple substances of Group 13 elements such as boron, aluminum, indium, gallium, and thallium; simple substances of Group 14 elements such as carbon, silicon, germanium, tin, and lead; simple substances of Group 15 elements such as phosphorus, arsenic, antimony, and bismuth; simple substances of Group 16 elements such as sulfur, selenium, and tellurium; sodium oxalate; active carbon; and cesium cobalt trifluoride. Preferred reducing agents are zinc, iron, copper, nickel, and palladium wherein zinc is more preferred. These reducing agents can be used individually or in combination. When zinc is used, it is used at 6.0 to 200 equivalents and preferably 50 to 100 equivalents with reference to the starting material.

The reaction is preferably run under a vacuum or under an inert gas atmosphere such as nitrogen, helium, neon, or argon. The reaction temperature is 0 to 600° C. and preferably 200° C. to 300° C. The reaction time is 1 to 110 hours and preferably 2 to 24 hours.

The defluorination step may be carried out using only starting material and reducing agent; however, other substances may also be present. Substances that act as a solvent or catalyst can be selected as the other, co-present substances. For example, the starting material can be reacted in an organic solvent with samarium iodide, zinc, sodium/benzophenone, or a combination thereof. The organic solvent can be exemplified by N,N-dimethylformamide and tetrahydrofuran.

After completion of the reaction, the target compound is obtained by execution of the usual work-up and then purification. The heretofore known procedures can be used for purification, including solvent extraction and recrystallization.

EXAMPLES

The present invention is specifically described below using examples, but the methods for synthesizing the novel compounds according to the present invention are not limited to these examples.

The melting points were measured in the examples using a Model B-540 from the Buchi Co. The NMR measurements were taken using a Gemini 200 NMR Spectrometer from the Varian Co. The mass analyses were carried out using a GCMS-QP5050A from Shimadzu. The elemental analyses were carried out using a CHN Corder Model MT-6 from Yanaco Bunseki Kogyo Co.

Example 1

Synthesis of 1,2,3,4,8,9,10,11-octafluoro-5,7,12,14-tetrahydroxypentacen-6,13-dione (3)

4,5,6,7-tetrafluoroisobenzofuran-1,3-dione (2) (5.75 g, 26.1 mmol), 5,6,7,8-tetrafluoro-9,10-dihydroxy-2,3-dihydroanthracen-1,4-dione (1) (9.84 g, 31.3 mmol), aluminum chloride (1.53 g, 11.5 mmol), and sodium chloride (10.0 g, 171 mmol) were added to a 200-mL SUS autoclave and heated for 1 hour at 280° C. After completion of the reaction, cooling to room temperature was carried out and the reaction mixture was then introduced into dilute hydrochloric acid and was stirred for 1 hour at 100° C. The mixture was then filtered and the residue was washed with methanol, dichloromethane, toluene, and ether in the sequence given. The resulting solid was vacuum dried to give 11.5 g (85% yield) 1,2,3,4,8,9,10,11-octafluoro-5,7,12,14-tetrahydroxypentacen-6,13-dione (3).

melting point: 300° C. (decomposition)
mass analysis (MS m/z): 516 (M$^+$, 100) 258 (29).

| elemental analysis | |
|---|---|
| calculated for C$_{22}$H$_4$F$_8$O$_6$: | C, 51.18; H, 0.78. |
| found: | C, 51.40; H, 1.07. |

Example 2

Synthesis of 1,2,3,4,5,5,6,6,7,7,8,9,10,11,12,12,13, 13,14,14-eicosafluoro-5,6,7,12,13,14-hexahydropentacene (7)

1,2,3,4,8,9,10,11-octafluoro-5,7,12,14-tetrahydroxypentacen-6,13-dione (5 g, 9.68 mmol) was introduced into a 500-mL SUS autoclave; the vessel was cooled to −78° C.; and hydrogen fluoride (100 g) and then sulfur tetrafluoride (25 g, 231 mmol) were added. Heating was thereafter carried out to 150° C. with the reaction vessel sealed. The pressure in the reaction vessel reached 4.0 MPa (gauge pressure) at this time. After reaction for 96 hours, the reaction vessel was slowly cooled to room temperature and the low-boiling compounds were gradually discarded into a detoxification apparatus. Nitrogen was introduced into the vessel when the internal pressure reached ambient pressure and the residual hydrogen fluoride was completely eliminated. The reaction product (6.6 g) was then extracted with 600 mL hot chloroform, and filtration and then concentration of the solution gave 4.8 g of a crude compound (7) product. 2.5 g (3.87 mmol, 40% yield) pure compound (7) was obtained by recrystallization of the crude compound (7) product from chloroform.
melting point: 267-269° C.
$^{19}$F NMR (188 MHz, solvent: CDCl$_3$, reference: C$_6$F$_6$). δ 70.91-70.73 (m, 8F) 64.64-64.46 (m, 4F) 25.86-25.66 (m, 4F) 16.70 (d, J=12.8 Hz, 4F).
mass analysis (MS m/z): 644 (M$^+$, 100) 625 (M$^+$-F, 32) 575 (M$^+$-CF$_3$, 77.2).

| elemental analysis | |
|---|---|
| calculated for C$_{22}$F$_{20}$: | C, 41.02. |
| found: | C, 40.96. |

The filtration residue was recovered to give 1.6 g (2.7 mmol, 28%) 1,2,3,4,5,5,7,7,8,9,10,11,12,12,14,14-hexadecafluoro-5,7,12,14-tetrahydropentacen-6,13-dione (17).
mass analysis (MS m/z): 600 (M$^+$, 100).

Example 3

Synthesis of 1,2,3,4,5,5,6,6,7,7,8,9,10,11,12,12,13, 13,14,14-eicosafluoro-5,6,7,12,13,14-hexahydropentacene (7)

1,2,3,4,8,9,10,11-octafluoro-5,7,12,14-tetrahydroxypentacen-6,13-dione (3) (10 g, 19.4 mmol) was introduced into a 500-mL Hastelloy C autoclave; the vessel was cooled to −78° C.; and hydrogen fluoride (100 g) and then sulfur tetrafluoride (36 g, 323 mmol) were added. Heating was thereafter carried out to 150° C. with the reaction vessel sealed. The pressure in the reaction vessel reached 4.0 MPa (gauge pressure) at this time. After reaction for 68 hours, the reaction vessel was slowly cooled to room temperature and the low-boiling compounds were gradually discarded into a detoxification apparatus. Nitrogen was introduced into the vessel when the internal pressure reached ambient pressure and the residual hydrogen fluoride was completely eliminated. The reaction product (13.3 g) was then extracted with 1.5 L hot chloroform, and filtration and then recrystallization gave 8.0 g (12.4 mmol, 64% yield) pure compound (7).
melting point: 267-269° C.
$^{19}$F NMR (188 MHz, solvent: CDCl$_3$, reference: C$_6$F$_6$). δ 70.91-70.73 (m, 8F) 64.64-64.46 (m, 4F) 25.86-25.66 (m, 4F) 16.70 (d, J=12.8 Hz, 4F).
mass analysis (MS m/z): 644 (M$^+$, 100) 625 (M$^+$-F, 32) 575 (M$^+$-CF$_3$, 77.2).

| elemental analysis | |
|---|---|
| calculated for C$_{22}$F$_{20}$: | C, 41.02. |
| found: | C, 40.96. |

The filtration residue was recovered to give 1.2 g (2 mmol, 10%) 1,2,3,4,5,5,7,7,8,9,10,11,12,12,14,14-hexadecafluoro-5,7,12,14-tetrahydropentacen-6,13-dione (17).
mass analysis (MS m/z): 600 (M$^+$, 100).

Example 4

Synthesis of 1,2,3,4,5,5,6,6,7,7,8,9,10,11,12,12,13, 13,14,14-eicosafluoro-5,6,7,12,13,14-hexahydropentacene (7)

1,2,3,4,5,5,7,7,8,9,10,11,12,12,14,14-hexadecafluoro-5,7,12,14-tetrahydropentacen-6,13-dione (17) (5.1 g, 8.5 mmol) was introduced into a 500-mL SUS autoclave; the vessel was cooled to −78° C.; and hydrogen fluoride (100 g) and then sulfur tetrafluoride (11 g, 102 mmol) were added. Heating was thereafter carried out to 150° C. with the reaction vessel sealed. The pressure in the reaction vessel reached 3.4 MPa (gauge pressure) at this time. After reaction for 66 hours, the reaction vessel was slowly cooled to room temperature and the low-boiling compounds were gradually discarded into a detoxification apparatus. Nitrogen was introduced into the vessel when the internal pressure reached ambient pressure and the residual hydrogen fluoride was completely eliminated. The reaction product (5.2 g) was then extracted with 600 mL hot chloroform, and filtration and then concentration of the solution gave 2.0 g crude compound (7) product. Recovery of the filtration residue gave 3.1 g (5.2 mmol, 61%) compound (17).

Example 5

Synthesis of 1,2,3,4,5,5,6,6,7,7,8,9,10,11,12,12,13, 13,14,14-eicosafluoro-5,6,7,12,13,14-hexahydropentacene (7)

1,2,3,4,5,5,7,7,8,9,10,11,12,12,14,14-hexadecafluoro-5,7,12,14-tetrahydropentacen-6,13-dione (17) (5.1 g, 8.5 mmol) was introduced into a 500-mL Hastelloy C autoclave; the vessel was cooled to −78° C.; and hydrogen fluoride (100 g) and then sulfur tetrafluoride (11 g, 102 mmol) were added. Heating was thereafter carried out to 150° C. with the reaction vessel sealed. The pressure in the reaction vessel reached 3.4 MPa (gauge pressure) at this time. After reaction for 60 hours, the reaction vessel was slowly cooled to room temperature and the low-boiling compounds were gradually discarded into a detoxification apparatus. Nitrogen was introduced into the vessel when the internal pressure reached ambient pressure and the residual hydrogen fluoride was completely eliminated. The reaction product (5.2 g) was then extracted with 600 mL hot chloroform, and filtration and then concentration of the solution gave 2.0 g crude compound (7) product. Recovery of the filtration residue gave 3.1 g (5.21 mmol, 61%) compound (17).

Example 6

Synthesis of tetradecafluoropentacene (9)

A mixture of 1,2,3,4,5,5,6,6,7,7,8,9,10,11,12,12,13,13,14,14-eicosafluoro-5,6,7,12,13,14-hexahydropentacene (7) (1.23 g, 1.91 mmol) and zinc (10.8 g, 165 mmol) was introduced into a glass tube (length=100 mm, outside diameter=26 mm); the tube was sealed under a vacuum; and heating was carried out for 30 minutes at 230° C. and then 3 hours at 280° C. The reaction mixture was stirred for 8 hours in 20% hydrochloric acid. The resulting suspension was filtered, and the residual solid was washed with dilute hydrochloric acid, water, and methanol in the sequence given to give a dark blue solid. Sublimation of this solid in vacuo at 280° C. gave 663 mg (1.25 mmol, 65% yield) tetradecafluoropentacene (9).

mass analysis (MS m/z): 530 ($M^+$, 100) 499 ($M^+$-CF, 25) 265 (51).

| elemental analysis | |
|---|---|
| calculated for $C_{22}F_{14}$: | C, 49.84. |
| found: | C, 49.56. |

Example 7

Synthesis of tetradecafluoropentacene (9)

A mixture of 1,2,3,4,5,5,6,6,7,7,8,9,10,11,12,12,13,13,14,14-eicosafluoro-5,6,7,12,13,14-hexahydropentacene (7) (1 g, 1.55 mmol) and zinc (4 g, 61.2 mmol) was introduced into a sealable SUS tube (length=10 cm, outside diameter=12 mm, equipped with a plug for closing the tube and connected to a Swagelok coupling); the interior was substituted with argon under ambient pressure; and the plug was fastened and the tube was sealed. Heating was subsequently carried out for 6 hours at 230° C. and then 21 hours at 260° C. After completion of the reaction, the reaction mixture was stirred for 8 hours in 20% hydrochloric acid. The resulting suspension was filtered, and the residual solid was washed with dilute hydrochloric acid, water, acetic acid, methanol, and diethyl ether in the sequence given to give a dark blue solid. Sublimation of this solid in vacuo at 280 to 300° C. gave 423 mg (0.798 mmol, 51% yield) tetradecafluoropentacene (9).

mass analysis (MS m/z): 530 ($M^+$, 100) 499 ($M^+$-CF, 25) 265 (51).

| elemental analysis | |
|---|---|
| calculated for $C_{22}F_{14}$: | C, 49.84. |
| found: | C, 49.56. |

Example 8

Synthesis of 5,5,6,7,7,12,12,13,14,14-decafluoro-5,7,12,14-tetrahydropentacene (8)

5,7,12,14-tetrahydroxypentacen-6,13-dione (6) (1 g, 2.68 mmol) was introduced into a 200-mL SUS autoclave; the vessel was cooled to −78° C.; and hydrogen fluoride (50 g) and then sulfur tetrafluoride (10 g, 93 mmol) were added. Heating was thereafter carried out to 150° C. with the reaction vessel sealed. The pressure in the reaction vessel reached 3.5 MPa (gauge pressure) at this time. After reaction for 20 hours, the reaction vessel was slowly cooled to room temperature and the low-boiling compounds were gradually discarded into a detoxification apparatus. Nitrogen was introduced into the vessel when the internal pressure reached ambient pressure and the residual hydrogen fluoride was completely eliminated. Mass analysis on the resulting product mixture (1.4 g) gave a purity of 90% for the compound (8).

$^1$H NMR (200 MHz, solvent: $CDCl_3$, reference: $Me_4Si$). δ 8.0-7.95 (m, 4H) 7.8-7.75 (m, 4H).

$^{19}$F NMR (188 MHz, solvent: $CDCl_3$, reference: $CFCl_3$). δ 81.2 (d, J=22.8 Hz, 8F) -114.3 (m, 2F).

mass analysis (MS m/z): 462 ($M^+$, 100).

Example 9

Synthesis of 6,6,13,13-tetrafluoro-6,13-dihydropentacene (15)

Pentacen-6,13-dione (14) (2 g, 6.49 mmol) was introduced into a 100-mL SUS autoclave; the vessel was cooled to −78° C.; and hydrogen fluoride (32 g) and then sulfur tetrafluoride (5.6 g, 51.7 mmol) were added. Heating was thereafter carried out to 100° C. with the reaction vessel sealed. The pressure in the reaction vessel reached 1.8 MPa (gauge pressure) at this time. After reaction for 6 hours, the reaction vessel was slowly cooled to room temperature and the low-boiling compounds were gradually discarded into a detoxification apparatus. Nitrogen was introduced into the vessel when the internal pressure reached ambient pressure and the residual hydrogen fluoride was completely eliminated. The reaction product was then extracted with 800 mL hot chlorobenzene, and the crude product mixture obtained by concentrating the filtrate was purified by silica gel column chromatography (developing solvent: chlorobenzene) to give 1.0 g (2.89 mmol, 40% yield) 6,6,13,13-tetrafluoro-6,13-dihydropentacene (15).

$^1$H NMR (200 MHz, solvent: $CDCl_3$, reference: $Me_4Si$). δ8.55 (s, 4H) 8.11-8.06 (m, 4H) 7.74-7.68 (m, 4H).

$^{19}$F NMR (188 MHz, solvent: $CDCl_3$, reference: $CFCl_3$). δ −83.1 (s, 4F).

mass analysis (MS m/z): 352 ($M^+$, 100).

| elemental analysis | |
|---|---|
| calculated for $C_{22}H_{12}F_4$: | C, 74.86; H, 3.85. |
| found: | C, 83.91; H, 3.42. |

Example 10

Synthesis of 6,6,13,13-tetrafluoro-6,13-dihydropentacene (15)

Pentacen-6,13-dione (14) (2 g, 6.49 mmol) was introduced into a 100-mL SUS autoclave; the vessel was cooled to −78° C.; and hydrogen fluoride (32 g) and then sulfur tetrafluoride (7.2 g, 66.5 mmol) were added. Heating was thereafter carried out to 70° C. with the reaction vessel sealed. The pressure in the reaction vessel reached 1.1 MPa (gauge pressure) at this time. After reaction for 6 hours, the reaction vessel was slowly cooled to room temperature and the low-boiling compounds were gradually discarded into a detoxification apparatus. Nitrogen was introduced into the vessel when the internal pressure reached ambient pressure and the residual hydrogen fluoride was completely eliminated, yielding 1.99 g of a mixture of 6,6,13,13-tetrafluoro-6,13-dihydropentacene (15) and 13,13-difluoro-13H-pentacen-6-one (19) ((15):(19)=1:3 (weight ratio)).

(19)
$^1$H NMR (200 MHz, solvent: CDCl$_3$, reference: Me$_4$Si). δ 8.98 (s, 2H) 8.6 (s, 2H) 8.18-8.05 (m, 4H) 7.78-7.68 (m, 4H).
$^{19}$F NMR (188 MHz, solvent: CDCl$_3$, reference: CFCl$_3$). δ −75.2 (s, 2F).
mass analysis (MS m/z): 330 (M$^+$, 100).

Example 11

Synthesis of 6,13-difluoropentacene (16)

6,6,13,13-tetrafluoro-6,13-dihydropentacene (15) (704 mg, 2.0 mmol) and 46 mL of a 0.1 mol/L samarium iodide/THF solution were introduced into a 300-mL three-neck glass flask equipped with a stirring bar, thermometer, rubber septum, and nitrogen seal and were heated under reflux for 7 hours while stirring. 1 M aqueous KOH solution (250 mL) was then added to stop the reaction, and stirring was continued in this condition for 1 hour. The resulting solution was filtered and the residual solid was washed with hydrochloric acid, water, and methanol in the order given. This was followed by washing with toluene for 5 hours using a Soxhlet extractor. After filtration, the filtrate was concentrated to give 335 mg of a dark blue solid. This was purified by sublimation (0.013 Pa, 250° C.) to give 72.5 mg (0.23 mmol, 11% yield) 6,13-difluoropentacene (16).

mass analysis (MS m/z): 314 (M$^+$, 100).

| elemental analysis | |
|---|---|
| calculated for C$_{22}$H$_{12}$F$_2$: | C, 84.06; H, 3.85. |
| found: | C, 83.91; H, 4.04. |

Example 12

Preparation of 5,5,7,7,12,12,14,14-octafluoro-5,7,12,14-tetrahydropentacene (12)

Pentacen-5,7,12,14-tetraone (11) (1 g, 3.0 mmol) was introduced into a 200-mL SUS autoclave; the vessel was cooled to −78° C.; and hydrogen fluoride (67 g) and then sulfur tetrafluoride (7.7 g, 71.5 mmol) were added. Heating was thereafter carried out to 100° C. with the reaction vessel sealed. The pressure in the reaction vessel reached 1.1 MPa (gauge pressure) at this time. After reaction for 20 hours, the reaction vessel was slowly cooled to room temperature and the low-boiling compounds were gradually discarded into a detoxification apparatus. Nitrogen was introduced into the vessel when the internal pressure reached ambient pressure and the residual hydrogen fluoride was completely eliminated, yielding 1.4 g of a mixture of 5,5,7,7,12,12,14,14-octafluoro-5,7,12,14-tetrahydropentacene (12) and 7,7,12,12,14,14-hexafluoro-7,14-dihydro-12H-pentacen-5-one (18) ((12):(18=8:2 (weight ratio)).

(12)
$^1$H NMR (200 MHz, solvent: CDCl$_3$, reference: Me$_4$Si). δ 8.5 (m, 2H) 8.0-7.9 (m, 4H) 7.8-7.7 (m, 4H).
$^{19}$F NMR (188 MHz, solvent: CDCl$_3$, reference: CFCl$_3$). δ −82.2 (s, 8F).
mass analysis (MS m/z): 426 (M$^+$, 100).

| elemental analysis | |
|---|---|
| calculated for C$_{22}$H$_{10}$F$_8$: | C, 61.98; H, 2.36. |
| found: | C, 61.85; H, 2.40. |

(18)
$^1$H NMR (200 MHz, solvent: CDCl$_3$, reference: Me$_4$Si). δ 8.91-8.87 (m) 8.57 (s) 8.42-8.33 (m) 8.06-7.78 (m).
$^{19}$F NMR (188 MHz, solvent: CDCl$_3$, reference: CFCl$_3$). δ −81.2 (s, 2F) −82.3 (s, 2F) −82.4 (s, 2F).
mass analysis (MS m/z): 404 (M$^+$, 100).

The invention claimed is:
1. A compound represented by formula [2]

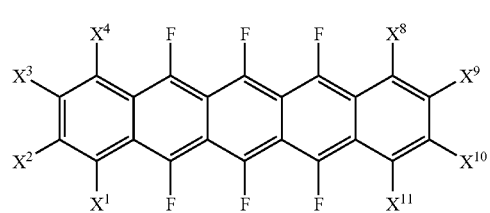

[2]

(wherein X$^1$, X$^2$, X$^3$, X$^4$, X$^8$, X$^9$, X$^{10}$, and X$^{11}$ represent fluorine, hydrogen, a substituted or unsubstituted C$_{1-8}$ alkyl group, a substituted or unsubstituted phenyl group, a substituted or unsubstituted naphthyl group, a substituted or unsubstituted anthracenyl group, a substituted or unsubstituted naphthacenyl group, or a substituted or unsubstituted pentacenyl group, and may be the same or different; or X$^2$ is bonded to X$^3$ to form a monocyclic or condensed polycyclic hydrocarbon group and/or X$^9$ is bonded to X$^{10}$ form a monocyclic or condensed polycyclic hydrocarbon group).

2. A compound represented by Formula [3]

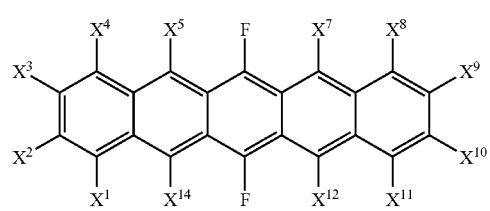

[3]

(wherein $X^1$, $X^2$, $X^3$, $X^4$, $X^5$, $X^7$, $X^8$, $X^9$, $X^{10}$, $X^{11}$, $X^{12}$, and $X^{14}$ represent fluorine, a substituted or unsubstituted $C_{1-8}$ alkyl group, a substituted or unsubstituted phenyl group, a substituted or unsubstituted naphthyl group, a substituted or unsubstituted anthracenyl group, a substituted or unsubstituted naphthacenyl group, or a substituted or unsubstituted pentacenyl group, and may be the same or different; or $X^2$ is bonded to $X^3$ to form a monocyclic or condensed polycyclic hydrocarbon group and/or $X^9$ is bonded to $X^{10}$ to form a monocyclic or condensed polycyclic hydrocarbon group).

3. A method of producing a compound represented by formula [13]

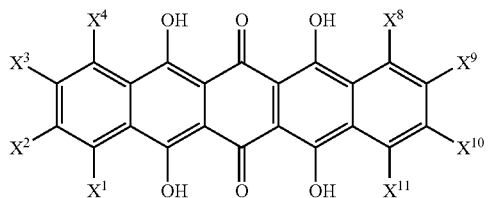

[13]

(wherein $X^1$, $X^2$, $X^3$, $X^4$, $X^8$, $X^9$, $X^{10}$, and $X^{11}$ represent fluorine, a substituted or unsubstituted $C_{1-8}$ alkyl group, a substituted or unsubstituted phenyl group, a substituted or unsubstituted naphthyl group, a substituted or unsubstituted anthracenyl group, a substituted or unsubstituted naphthacenyl group, or a substituted or unsubstituted pentacenyl group, and may be the same or different; or $X^2$ is bonded to $X^3$ to form a monocyclic or condensed polycyclic hydrocarbon group and/or $X^9$ is bonded to $X^{10}$ to form a monocyclic or condensed polycyclic hydrocarbon group), comprising the step of producing a compound represented by formula [13] by reacting a compound represented by formula [11]

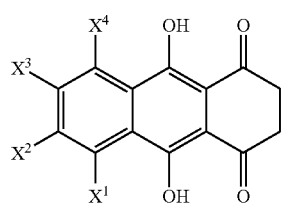

[11]

(wherein $X^1$, $X^2$, $X^3$, and $X^4$ represent fluorine, a substituted or unsubstituted C1-8 alkyl group, a substituted or unsubstituted phenyl group, a substituted or unsubstituted naphthyl group, a substituted or unsubstituted anthracenyl group, a substituted or unsubstituted naphthacenyl group, or a substituted or unsubstituted pentacenyl group, and may be the same or different; or $X^2$ is bonded to $X^3$ to form a monocyclic or condensed polycyclic hydrocarbon group) with a compound represented by formula [12]

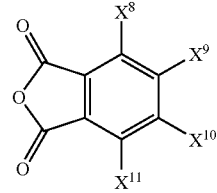

[12]

(wherein $X^8$, $X^9$, $X^{10}$, and $X^{11}$ represent fluorine, a substituted or unsubstituted $C_{1-8}$ alkyl group, a substituted or unsubstituted phenyl group, a substituted or unsubstituted naphthyl group, a substituted or unsubstituted anthracenyl group, a substituted or unsubstituted naphthacenyl group, or a substituted or unsubstituted pentacenyl group, and may be the same or different; or $X^9$ is bonded to $X^{10}$ to form a monocyclic or condensed polycyclic hydrocarbon group) in the presence of a Lewis acid.

4. The production method according to claim 3, wherein the Lewis acid comprises aluminum chloride.

5. A method of producing a compound represented by formula [14]

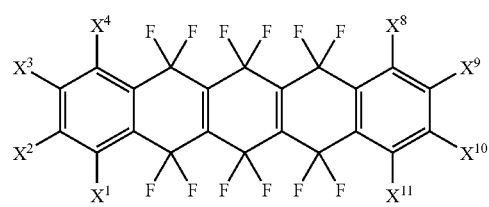

[14]

(wherein $X^1$, $X^2$, $X^3$, $X^4$, $X^8$, $X^9$, $X^{10}$, and $X^{11}$ are defined as for formula [13]), comprising the step of producing a compound represented by formula [14] by reacting a compound represented by formula [13]

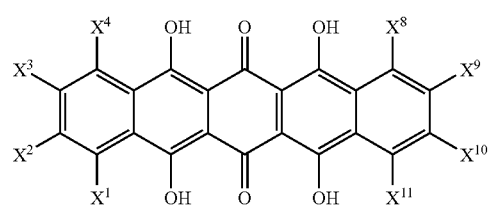

[13]

(wherein $X^1$, $X^2$, $X^3$, $X^4$, $X^8$, $X^9$, $X^{10}$, and $X^{11}$ represent fluorine, hydrogen, a substituted or unsubstituted $C_1$-8 alkyl group, a substituted or unsubstituted phenyl group, a substituted or unsubstituted naphthyl group, a substituted or unsubstituted anthracenyl group, a substituted or unsubstituted naphthacenyl group, or a substituted or unsubstituted pentacenyl group, and may be the same or different; or $X^2$ is bonded to $X^3$ to form a monocyclic or condensed polycyclic hydrocarbon group and/or $X^9$ is bonded to $X^{10}$ form a monocyclic or condensed polycyclic hydrocarbon group) with a fluorinating agent.

6. A method of producing a compound represented by formula [15]

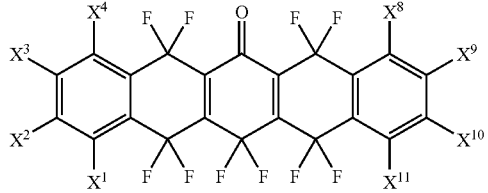

(wherein $X^1$, $X^2$, $X^3$, $X^4$, $X^8$, $X^9$, $X^{10}$, and $X^{11}$ are defined as for formula [13]), comprising the step of
producing a compound represented by formula [15] by reacting a compound represented by formula [13]

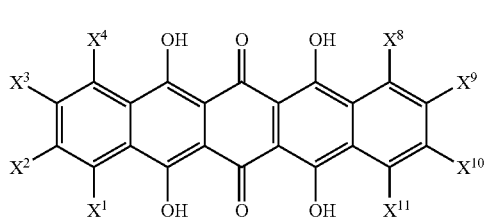

(wherein $X^1$, $X^2$, $X^3$, $X^4$, $X^8$, $X^9$, $X^{10}$, and $X^{11}$ represent fluorine, hydrogen, a substituted or unsubstituted $C_{1-8}$ alkyl group, a substituted or unsubstituted phenyl group, a substituted or unsubstituted naphthyl group, a substituted or unsubstituted anthracenyl group, a substituted or unsubstituted naphthacenyl group, or a substituted or unsubstituted pentacenyl group, and may be the same or different; or $X^2$ is bonded to $X^3$ to form a monocyclic or condensed polycyclic hydrocarbon group and/or $X^9$ is bonded to $X^{10}$ form a monocyclic or condensed polycyclic hydrocarbon group) with a fluorinating agent.

7. A method of producing a compound represented by formula [14]

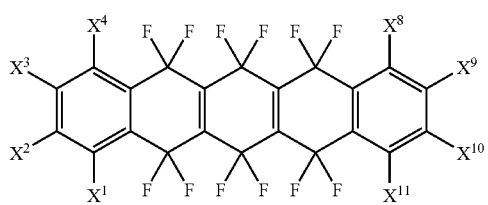

(wherein $X^1$, $X^2$, $X^3$, $X^4$, $X^8$, $X^9$, $X^{10}$, and $X^{11}$ are defined as for formula [15]), comprising the step of
producing a compound represented by formula [14] by reacting a compound represented by formula [15]

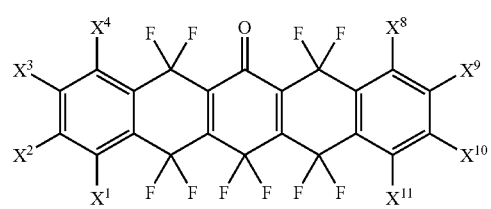

(wherein $X^1$, $X^2$, $X^3$, $X^4$, $X^8$, $X^9$, $X^{10}$, and $X^{11}$ represent fluorine, hydrogen, a substituted or unsubstituted $C_{1-8}$ alkyl group, a substituted or unsubstituted phenyl group, a substituted or unsubstituted naphthyl group, a substituted or unsubstituted anthracenyl group, a substituted or unsubstituted naphthacenyl group, or a substituted or unsubstituted pentacenyl group, and may be the same or different; or $X^2$ is bonded to $X^3$ to form a monocyclic or condensed polycyclic hydrocarbon group and/or $X^9$ is bonded to $X^{10}$ form a monocyclic or condensed polycyclic hydrocarbon group) with a fluorinating agent.

8. A method of producing a compound represented by formula [16]

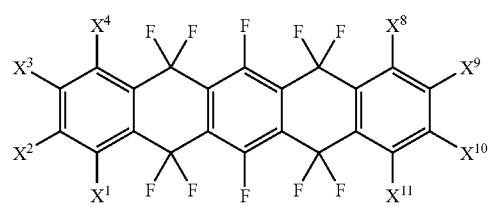

(wherein $X^1$, $X^2$, $X^3$, $X^4$, $X^8$, $X^9$, $X^{10}$, and $X^{11}$ are defined as for formula [13]), comprising the step of
producing a compound represented by formula [16] by reacting a compound represented by formula [13]

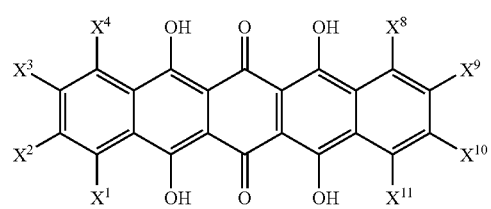

(wherein $X^1$, $X^2$, $X^3$, $X^4$, $X^8$, $X^9$, $X^{10}$, and $X^{11}$ represent fluorine, hydrogen, a substituted or unsubstituted $C_{1-8}$ alkyl group, a substituted or unsubstituted phenyl group, a substituted or unsubstituted naphthyl group, a substituted or unsubstituted anthracenyl group, a substituted or unsubstituted naphthacenyl group, or a substituted or unsubstituted pentacenyl group, and may be the same or different; or $X^2$ is bonded to $X^3$ to form a monocyclic or condensed polycyclic hydrocarbon group and/or $X^9$ is bonded to $X^{10}$ form a monocyclic or condensed polycyclic hydrocarbon group) with a fluorinating agent.

9. The production method according to any of claims 5 to 8, wherein the fluorinating agent comprises sulfur tetrafluoride.

10. A method of producing a compound represented by formula [2]

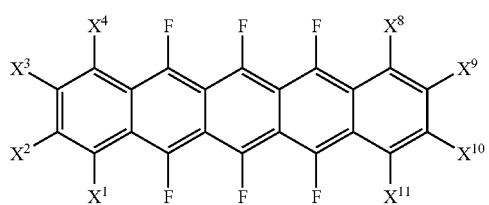

(wherein $X^1$, $X^2$, $X^3$, $X^4$, $X^8$, $X^9$, $X^{10}$, and $X^{11}$ are defined as for formula [14]), comprising the step of producing a compound represented by formula [2] by reacting a compound represented by formula [14]

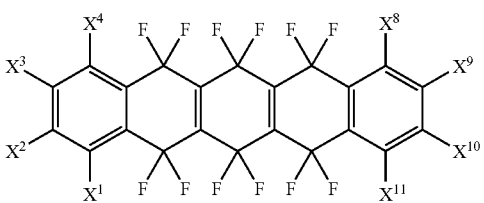

(wherein $X^1$, $X^2$, $X^3$, $X^4$, $X^8$, $X^9$, $X^{10}$, and $X^{11}$ represent fluorine, hydrogen, a substituted or unsubstituted $C_{1-8}$ alkyl group, a substituted or unsubstituted phenyl group, a substituted or unsubstituted naphthyl group, a substituted or unsubstituted anthracenyl group, a substituted or unsubstituted naphthacenyl group, or a substituted or unsubstituted pentacenyl group, and may be the same or different; or $X^2$ is bonded to $X^3$ to form a monocyclic or condensed polycyclic hydrocarbon group and/or $X^9$ is bonded to $X^{10}$ form a monocyclic or condensed polycyclic hydrocarbon group) with a reducing agent.

11. A method of producing a compound represented by formula [2]

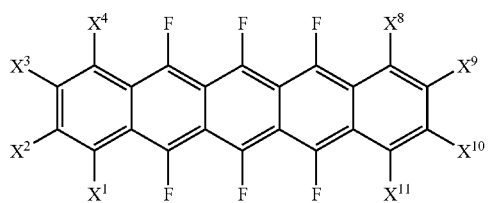

(wherein $X^1$, $X^2$, $X^3$, $X^4$, $X^8$, $X^9$, $X^{10}$, and $X^{11}$ are defined as for formula [16]), comprising the step of producing a compound represented by formula [2] by reacting a compound represented by formula [16]

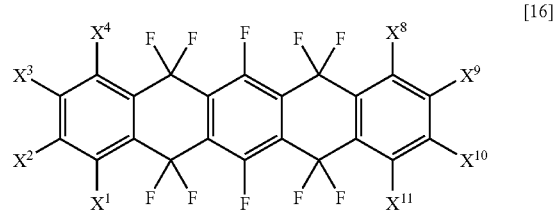

(wherein $X^1$, $X^2$, $X^3$, $X^4$, $X^8$, $X^9$, $X^{10}$, and $X^{11}$ represent fluorine, hydrogen, a substituted or unsubstituted $C_{1-8}$ alkyl group, a substituted or unsubstituted phenyl group, a substituted or unsubstituted naphthyl group, a substituted or unsubstituted anthracenyl group, a substituted or unsubstituted naphthacenyl group, or a substituted or unsubstituted pentacenyl group, and may be the same or different; or $X^2$ is bonded to $X^3$ to form a monocyclic or condensed polycyclic hydrocarbon group and/or $X^9$ is bonded to $X^{10}$ form a monocyclic or condensed polycyclic hydrocarbon group) with a reducing agent.

12. The production method according to claim 10 or 11, wherein the reducing agent comprises zinc, iron, copper, nickel, palladium, or a combination thereof.

13. A compound represented by formula

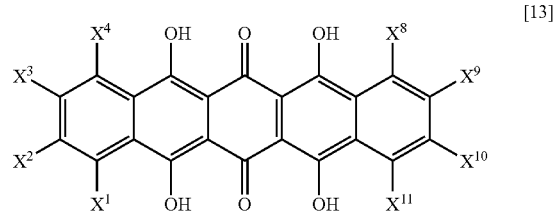

(wherein $X^1$, $X^2$, $X^3$, $X^4$, $X^8$, $X^9$, $X^{10}$, and $X^{11}$ represent fluorine, a substituted or unsubstituted $C_{1-8}$ alkyl group, a substituted or unsubstituted phenyl group, a substituted or unsubstituted naphthyl group, a substituted or unsubstituted anthracenyl group, a substituted or unsubstituted naphthacenyl group, or a substituted or unsubstituted pentacenyl group, and may be the same or different; or $X^2$ is bonded to $X^3$ to form a monocyclic or condensed polycyclic hydrocarbon group and/or $X^9$ is bonded to $X^{10}$ to form a monocyclic or condensed polycyclic hydrocarbon group).

14. A compound represented by formula [14]

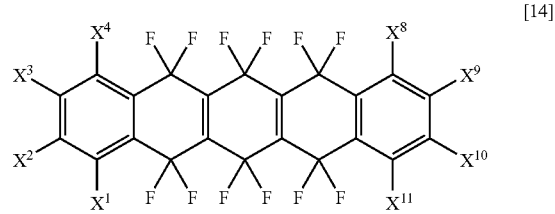

(wherein $X^1$, $X^2$, $X^3$, $X^4$, $X^8$, $X^9$, $X^{10}$, and $X^{11}$ represent fluorine, a substituted or unsubstituted $C_{1-8}$ alkyl group, a substituted or unsubstituted phenyl group, a substituted or unsubstituted naphthyl group, a substituted or unsubstituted anthracenyl group, a substituted or unsubstituted naphthacenyl group, or a substituted or unsubstituted pentacenyl group, and may be the same or different; or $X^2$ is bonded to $X^3$ to form a monocyclic or condensed polycyclic hydrocarbon group and/or $X^9$ is bonded to $X^{10}$ to form a monocyclic or condensed polycyclic hydrocarbon group).

15. A compound represented by formula [15]

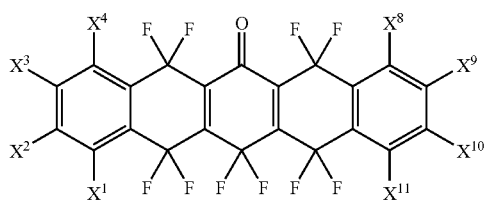

[15]

(wherein $X^1$, $X^2$, $X^3$, $X^4$, $X^8$, $X^9$, $X^{10}$, and $X^{11}$ represent fluorine, hydrogen, a substituted or unsubstituted $C_{1-8}$ alkyl group, a substituted or unsubstituted phenyl group, a substituted or unsubstituted naphthyl group, a substituted or unsubstituted anthracenyl group, a substituted or unsubstituted naphthacenyl group, or a substituted or unsubstituted pentacenyl group, and may be the same or different; or $X^2$ is bonded to $X^3$ to form a monocyclic or condensed polycyclic hydrocarbon group and/or $X^9$ is bonded to $X^{10}$ form a monocyclic or condensed polycyclic hydrocarbon group).

16. A compound represented by formula ]16]

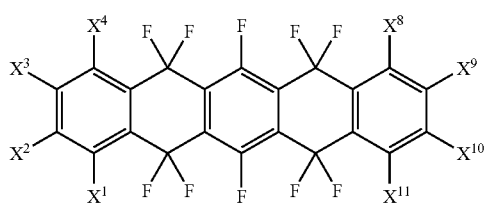

[16]

(wherein $X^1$, $X^2$, $X^3$, $X^4$, $X^8$, $X^9$, $X^{10}$, and $X^{11}$ represent fluorine, hydrogen, a substituted or unsubstituted $C_{1-8}$ alkyl group, a substituted or unsubstituted phenyl group, a substituted or unsubstituted naphthyl group, a substituted or unsubstituted anthracenyl group, a substituted or unsubstituted naphthacenyl group, or a substituted or unsubstituted pentacenyl group, and may be the same or different; or $X^2$ is bonded to $X^3$ to form a monocyclic or condensed polycyclic hydrocarbon group and/or $X^9$ is bonded to $X^{10}$ form a monocyclic or condensed polycyclic hydrocarbon group).

17. A method of producing a compound represented by formula [22]

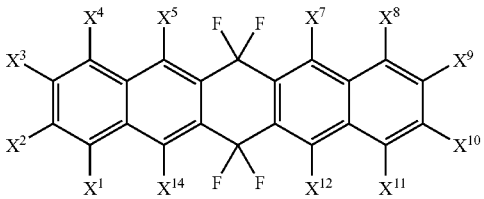

[22]

(wherein $X^1$, $X^2$, $X^3$, $X^4$, $X^5$, $X^7$, $X^8$, $X^9$, $X^{10}$, $X^{11}$, $X^{12}$, and $X^{14}$ are defined as for formula [21]), comprising the step of producing a compound represented by formula [22] by reacting a compound represented by formula [21]

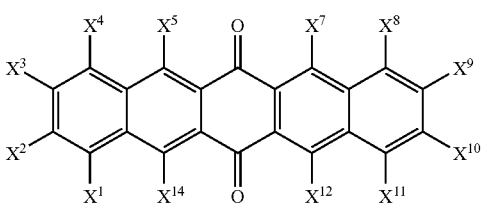

[21]

(wherein $X^1$, $X^2$, $X^3$, $X^4$, $X^5$, $X^7$, $X^8$, $X^9$, $X^{10}$, $X^{11}$, $X^{12}$, and $X^{14}$ represent fluorine, hydrogen, a substituted or unsubstituted $C_{1-8}$ alkyl group, a substituted or unsubstituted phenyl group, a substituted or unsubstituted naphthyl group, a substituted or unsubstituted anthracenyl group, a substituted or unsubstituted naphthacenyl group, or a substituted or unsubstituted pentacenyl group, and may be the same or different; or $X^2$ is bonded to $X^3$ to form a monocyclic or condensed polycyclic hydrocarbon group and/or $X^9$ is bonded to $X^{10}$ form a monocyclic or condensed polycyclic hydrocarbon group) with a fluorinating agent.

18. A method of producing a compound represented by formula [23]

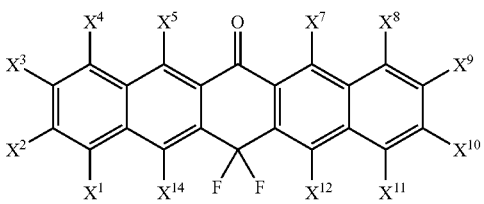

[23]

(wherein $X^1$, $X^2$, $X^3$, $X^4$, $X^5$, $X^7$, $X^8$, $X^9$, $X^{10}$, $X^{11}$, $X^{12}$, and $X^{14}$ are defined as for formula [21]), comprising the step of producing a compound represented by formula [23] by reacting a compound represented by formula [21]

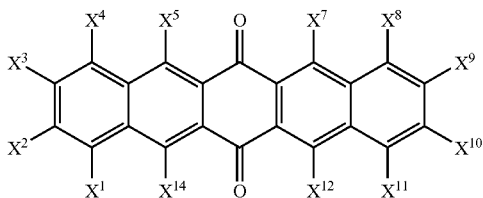

(wherein $X^1, X^2, X^3, X^4, X^5, X^7, X^8, X^9, X^{10}, X^{11}, X^{12}$, and $X^{14}$ represent fluorine, hydrogen, a substituted or unsubstituted $C_{1-8}$ alkyl group, a substituted or unsubstituted phenyl group, a substituted or unsubstituted naphthyl group, a substituted or unsubstituted anthracenyl group, a substituted or unsubstituted naphthacenyl group, or a substituted or unsubstituted pentacenyl group, and may be the same or different; or $X^2$ is bonded to $X^3$ to form a monocyclic or condensed polycyclic hydrocarbon group and/or $X^9$ is bonded to $X^{10}$ to form a monocyclic or condensed polycyclic hydrocarbon group) with a fluorinating agent.

19. A method of producing a compound represented by formula [22]

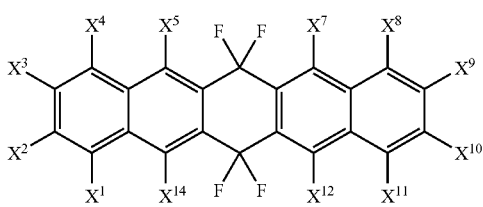

(wherein $X^1, X^2, X^3, X^4, X^5, X^7, X^8, X^9, X^{10}, X^{11}, X^{12}$, and $X^{14}$ are defined as for formula [23]), comprising the step of producing a compound represented by formula [22] by reacting a compound represented by formula [23]

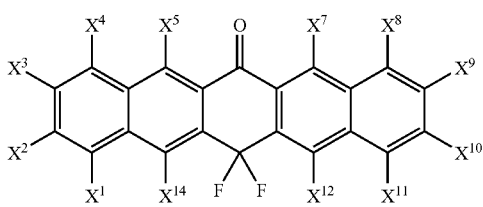

(wherein $X^1, X^2, X^3, X^4, X^5, X^7, X^8, X^9, X^{10}, X^{11}, X^{12}$, and $X^{14}$ represent fluorine, hydrogen, a substituted or unsubstituted $C_{1-8}$ alkyl group, a substituted or unsubstituted phenyl group, a substituted or unsubstituted naphthyl group, a substituted or unsubstituted anthracenyl group, a substituted or unsubstituted naphthacenyl group, or a substituted or unsubstituted pentacenyl group, and may be the same or different; or $X^2$ is bonded to $X^3$ to form a monocyclic or condensed polycyclic hydrocarbon group and/or $X^9$ is bonded to $X^{10}$ form a monocyclic or condensed polycyclic hydrocarbon group) with a fluorinating agent.

20. The production method according to any of claims 17 to 19, wherein the fluorinating agent comprises sulfur tetrafluoride.

21. A method of producing a compound represented by formula [3]

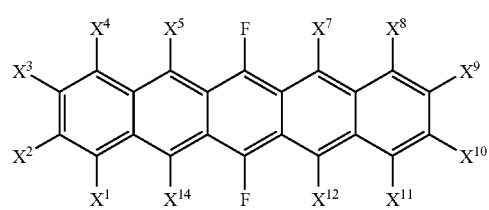

(wherein $X^1, X^2, X^3, X^4, X^5, X^7, X^8, X^9, X^{10}, X^{11}, X^{12}$, and $X^{14}$ are defined as for formula [22]), comprising the step of producing a compound represented by formula [3] by reacting a compound represented by formula [22]

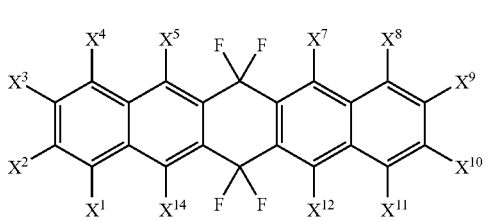

(wherein $X^1, X^2, X^3, X^4, X^5, X^7, X^8, X^9, X^{10}, X^{11}, X^{12}$, and $X^{14}$ represent fluorine, hydrogen, a substituted or unsubstituted $C_{1-8}$ alkyl group, a substituted or unsubstituted phenyl group, a substituted or unsubstituted naphthyl group, a substituted or unsubstituted anthracenyl group, a substituted or unsubstituted naphthacenyl group, or a substituted or unsubstituted pentacenyl group, and may be the same or different; or $X^2$ is bonded to $X^3$ to form a monocyclic or condensed polycyclic hydrocarbon group and/or $X^9$ is bonded to $X^{10}$ form a monocyclic or condensed polycyclic hydrocarbon group) with a reducing agent.

22. The production method according to claim 21, wherein the reducing agent comprises zinc, iron, copper, nickel, palladium, or a combination thereof.

23. A compound represented by formula

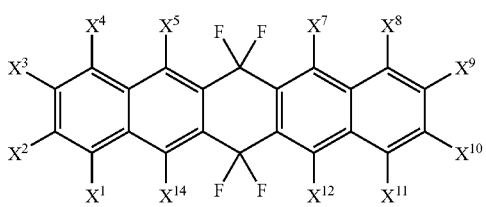

(wherein $X^1, X^2, X^3, X^4, X^5, X^7, X^8, X^9, X^{10}, X^{11}, X^{12}$, and $X^{14}$ represent fluorine, hydrogen, a substituted or unsubstituted $C_{1-8}$ alkyl group, a substituted or unsubstituted phenyl group, a substituted or unsubstituted naphthyl group, a substituted or unsubstituted anthracenyl group, a substituted or unsubstituted naphthacenyl group, or a substituted or unsubstituted pentacenyl group, and may be the same or different; or $X^2$ is bonded to $X^3$ to form a monocyclic or condensed polycyclic hydrocarbon group and/or $X^9$ is bonded to $X^{10}$ form a monocyclic or condensed polycyclic hydrocarbon group).

24. A compound represented by formula [23]

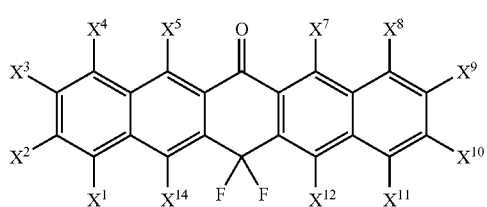

[23]

(wherein $X^1, X^2, X^3, X^4, X^5, X^7, X^8, X^9, X^{10}, X^{11}, X^{12}$, and $X^{14}$ represent fluorine, hydrogen, a substituted or unsubstituted $C_{1-8}$ alkyl group, a substituted or unsubstituted phenyl group, a substituted or unsubstituted naphthyl group, a substituted or unsubstituted anthracenyl group, a substituted or unsubstituted naphthacenyl group, or a substituted or unsubstituted pentacenyl group, and may be the same or different; or $X^2$ is bonded to $X^3$ to form a monocyclic or condensed polycyclic hydrocarbon group and/or $X^9$ is bonded to $X^{10}$ form a monocyclic or condensed polycyclic hydrocarbon group).

25. A method of producing a compound represented by formula [32]

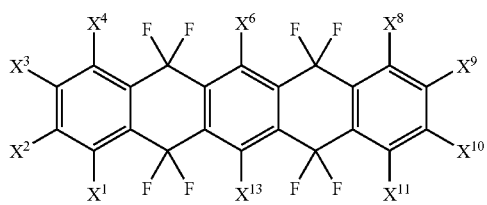

[32]

(wherein $X^1, X^2, X^3, X^4, X^6, X^8, X^9, X^{10}, X^{11}$, and $X^{13}$ are defined as for formula [31]), comprising the step of producing a compound represented by formula [32] by reacting a compound represented by formula [31]

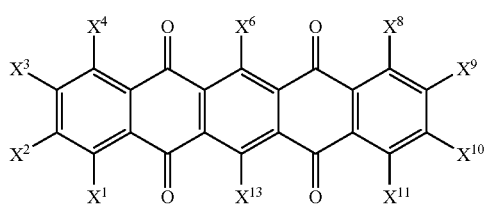

[31]

(wherein $X^1, X^2, X^3, X^4, X^6, X^8, X^9, X^{10}, X^{11}$, and $X^{13}$ represent fluorine, hydrogen, a substituted or unsubstituted $C_{1-8}$ group, a substituted or unsubstituted phenyl group, a substituted or unsubstituted naphthyl group, a substituted or unsubstituted anthracenyl group, a substituted or unsubstituted naphthacenyl group, or a substituted or unsubstituted pentacenyl group, and may be the same or different; or $X^2$ is bonded to $X^3$ to form a monocyclic or condensed polycyclic hydrocarbon group and/or $X^9$ is bonded to $X^{10}$ form a monocyclic or condensed polycyclic hydrocarbon group) with a fluorinating agent.

26. A method of producing a compound represented by formula [33]

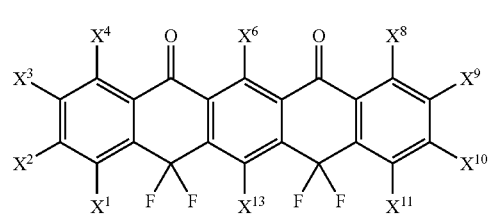

[33]

(wherein $X^1, X^2, X^3, X^4, X^6, X^8, X^9, X^{10}, X^{11}$, and $X^{13}$ are defined as for formula [31]), comprising the step of producing a compound represented by formula [33] by reacting a compound represented by formula [31]

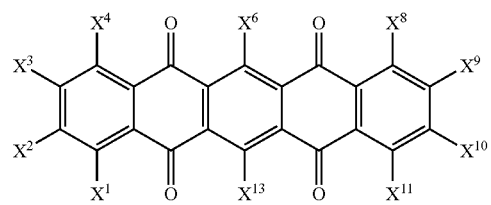

[31]

(wherein $X^1$, $X^2$, $X^3$, $X^4$, $X^6$, $X^8$, $X^9$, $X^{10}$, $X^{11}$, and $X^{13}$ represent fluorine, hydrogen, a substituted or unsubstituted $C_{1-8}$ alkyl group, a substituted or unsubstituted phenyl group, a substituted or unsubstituted naphthyl group, a substituted or unsubstituted anthracenyl group, a substituted or unsubstituted naphthacenyl group, or a substituted or unsubstituted pentacenyl group, and may be the same or different; or $X^2$ is bonded to $X^3$ to form a monocyclic or condensed polycyclic hydrocarbon group and/or $X^9$ is bonded to $X^{10}$ to form a monocyclic or condensed polycyclic hydrocarbon group) with a fluorinating agent.

27. A method of producing a compound represented by formula [32]

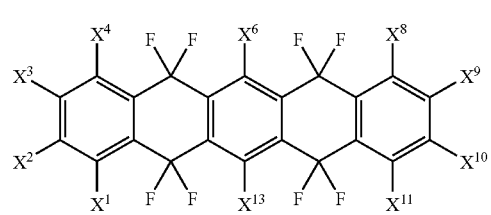

[32]

(wherein $X^1, X^2, X^3, X^4, X^6, X^8, X^9, X^{10}, X^{11}$, and $X^{13}$ are defined as for formula [33]), comprising the step of producing a compound represented by formula [32] by reacting a compound represented by formula [33]

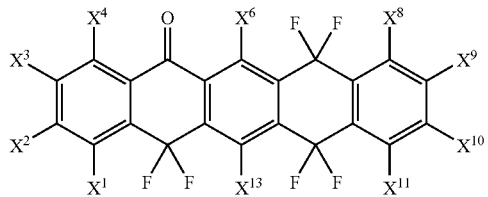

(wherein $X^1$, $X^2$, $X^3$, $X^4$, $X^6$, $X^8$, $X^9$, $X^{10}$, $X^{11}$, and $X^{13}$ represent fluorine, hydrogen, a substituted or unsubstituted $C_{1-8}$ alkyl group, a substituted or unsubstituted phenyl group, a substituted or unsubstituted naphthyl group, a substituted or unsubstituted anthracenyl group, a substituted or unsubstituted naphthacenyl group, or a substituted or unsubstituted pentacenyl group, and may be the same or different; or $X^2$ is bonded to $X^3$ to form a monocyclic or condensed polycyclic hydrocarbon group and/or $X^9$ is bonded to $X^{10}$ to form a monocyclic or condensed polycyclic hydrocarbon group) with a fluorinating agent.

28. The production method according to any of claims 25 to 27, wherein the fluorinating agent comprises sulfur tetrafluoride.

29. A method of producing a compound represented by formula [4]

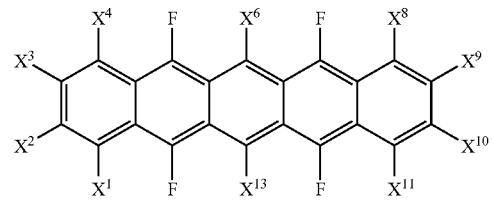

(wherein $X^1$, $X^2$, $X^3$, $X^4$, $X^6$, $X^8$, $X^9$, $X^{10}$, $X^{11}$, and $X^{13}$ are defined as for formula [32]), comprising the step of producing a compound represented by formula [4] by reacting a compound represented by formula [32]

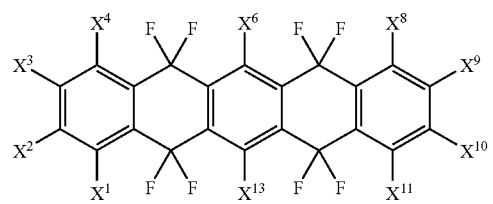

(wherein $X^1$, $X^2$, $X^3$, $X^4$, $X^6$, $X^8$, $X^9$, $X^{10}$, $X^{11}$, and $X^{13}$ represent fluorine, hydrogen, a substituted or unsubstituted $C_{1-8}$ alkyl group, a substituted or unsubstituted phenyl group, a substituted or unsubstituted naphthyl group, a substituted or unsubstituted anthracenyl group, a substituted or unsubstituted naphthacenyl group, or a substituted or unsubstituted pentacenyl group, and may be the same or different; or $X^2$ is bonded to $X^3$ to form a monocyclic or condensed polycyclic hydrocarbon group and/or $X^9$ is bonded to $X^{10}$ form a monocyclic or condensed polycyclic hydrocarbon group) with a reducing agent.

30. The production method according to claim 29, wherein the reducing agent comprises zinc, iron, copper, nickel, palladium, or a combination thereof.

31. A compound represented by formula [32]

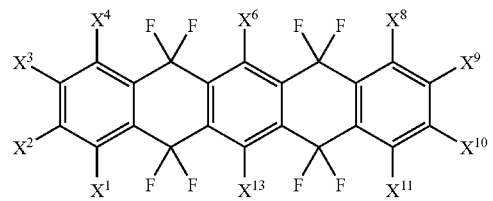

(wherein $X^1$, $X^2$, $X^3$, $X^4$, $X^6$, $X^8$, $X^9$, $X^{10}$, $X^{11}$, and $X^{13}$ represent fluorine, hydrogen, a substituted or unsubstituted $C_{1-8}$ alkyl group, a substituted or unsubstituted phenyl group, a substituted or unsubstituted naphthyl group, a substituted or unsubstituted anthracenyl group, a substituted or unsubstituted naphthacenyl group, or a substituted or unsubstituted pentacenyl group, and may be the same or different; or $X^2$ is bonded to $X^3$ to form a monocyclic or condensed polycyclic hydrocarbon group and/or $X^9$ is bonded to $X^{10}$ form a monocyclic or condensed polycyclic hydrocarbon group).

* * * * *